United States Patent

Suenaga et al.

[11] Patent Number: 6,115,891
[45] Date of Patent: Sep. 12, 2000

[54] CONTINUOUS SURFACE FASTENER TAPE AND METHOD OF MANUFACTURING THE SAME

[75] Inventors: Tomohiro Suenaga, Nara; Ryuichi Murasaki, Toyama, both of Japan

[73] Assignee: YKK Corporation, Tokyo, Japan

[21] Appl. No.: 08/919,807

[22] Filed: Aug. 29, 1997

[30] Foreign Application Priority Data

Aug. 30, 1996 [JP] Japan .................................. 8-229607
Jun. 30, 1997 [JP] Japan .................................. 9-174248

[51] Int. Cl.⁷ .............................. A44B 18/00; B32B 3/00
[52] U.S. Cl. ................................ 24/442; 24/304; 24/452; 24/DIG. 11
[58] Field of Search ............................ 24/304, 442, 452, 24/DIG. 11

[56] References Cited

U.S. PATENT DOCUMENTS

| 758,923 | 5/1904 | Knowlton et al. ................. 24/DIG. 11 |
| 2,096,352 | 10/1937 | Semonsen ......................... 24/DIG. 11 |
| 2,205,956 | 6/1940 | Humphner ........................ 24/DIG. 11 |
| 2,329,527 | 9/1943 | Golub ................................ 24/DIG. 11 |
| 2,975,538 | 3/1961 | Murfin ....................................... 24/304 |
| 3,370,818 | 2/1968 | Perr ............................................. 24/442 |
| 3,950,824 | 4/1976 | Karami ............................. 24/DIG. 115 |
| 4,020,842 | 5/1977 | Richman et al. .................. 24/DIG. 11 |
| 4,382,303 | 5/1983 | Lunt . |
| 4,894,080 | 1/1990 | Nestegard ................................ 24/442 |
| 5,282,914 | 2/1994 | Spendlove ................................ 24/304 |
| 5,537,722 | 7/1996 | Niederhofer et al. .................... 24/304 |

FOREIGN PATENT DOCUMENTS 0 324 578  7/1989  European Pat. Off. .
WO 94/23610 10/1994  WIPO .

*Primary Examiner*—Victor N. Sakran
*Attorney, Agent, or Firm*—Hill & Simpson

[57] ABSTRACT

In manufacturing a continuous surface fastener tape on an injection molding machine, a male engaging portion is injection molded on one surface of a continuous substrate sheet of thermoplastic resin at one longitudinal margin, and an adhesive agent is applied to the other surface of the substrate sheet at the other longitudinal margin to form an adhesive layer. The surface fastener tape is stored in superposed form, such as in roll or in stack, and can be out into individual surface fastener pieces for use as it is demanded. In production, molten resin is continuously injected to the die wheel from an injection nozzle to mold the continuous surface fastener tape, and the adhesive layer is formed on the surface fastener tape using an adhesive-agent applicator.

16 Claims, 22 Drawing Sheets

CONTINUOUS SURFACE FASTENER TAPE AND METHOD OF MANUFACTURING THE SAME

BACKGROUND OF THE INVENTION

1. Field of the Invention

This invention relates to an inexpensive surface fastener to be used as fasteners for disposable paper diapers or other products, and more particularly to a continuous surface fastener tape having hook-shape engaging portions adapted to be cut into individual surface fastener pieces.

2. Description of the Related Art

FIG. 30 of the accompanying drawings shows a conventional fastener for a diaper, etc. In this fastener, a plastic substrate piece 5' has on one surface an adhesive layer 6' extending from the center to one end and a protective separating portion 7' extending from the center to the other end. On the other surface, the plastic substrate sheet has another adhesive layer 6' and another protective separating portion 7' arranged reversely to the one surface. The plastic substrate sheet 5' is folded double when attaching to one part of a diaper A' in production of diapers, and in use the adhesive layer 6' is peeled off the corresponding protective separating portion 7' and is then attached to a companion part of the diaper A'. This part is exemplified by Japanese Utility Model Publication No. Hei 1-29230.

The concept of using a surface fastener in a disposable diaper is disclosed in Japanese Patent Laid-Open Publication No. Hei 2-5947. In this surface fastener, as shown in FIG. 31 of the accompanying drawings, a multiplicity of elastic engaging elements 4' are arranged on one surface of a thin, very flexible substrate sheet 5', each engaging element 4' having a round-surfaced head 4'-1 and an upright stem 4'-2 standing on the substrate sheet 5'. This surface fastener is fixed to an end portion of a narrow flexible, rectangular high-polymer tab, which is equipped with a low-viscosity pressure-sensitive adhesive agent to keep the tab in folded form so that the tab may be unfolded or peeled off for engagement with a companion surface fastener when the diaper is in use.

With the plastic substrate piece 5' disclosed in the first-named publication, since the diaper A' is fastened by the adhesive layer 6', only a limited degree of attaching strength can be achieved. This plastic substrate piece 5' is difficult either to manufacture continuously or to store in continuous form, causing a laborious inventory management.

The surface fastener disclosed in the second-named publication requires a very complex manufacturing process, which is laborious and time-consuming. Further, since the surface fastener and the high-polymer tab cannot be formed at once by extrusion molding, a high degree of manufacturing efficiency and hence a low price of products cannot be realized.

SUMMARY OF THE INVENTION

With the foregoing problems in view, it is a first object of this invention to provide a continuous-length surface fastener tape which can be attached to products such as paper diapers or the like and which can be stored in continuous form and is adapted to be simply cut into individual surface fastener pieces for attachment to the diapers in diaper production.

A second object of the invention is to provide a surface fastener tape which is adapted to be cut into individual surface fastener pieces fit to various kinds of diapers or the like so that the individual surface fastener pieces can be attached simply to front and back sides of a paper diaper or the like by specifying the arrangement of the surface fastener and an adhesive layer for attaching the surface fastener to the paper diaper or the like.

A third object of the invention is to provide a surface fastener tape in which an adhesive layer to facilitate attaching the individual surface fastener piece to a paper diaper or the like can be formed by a very simple process.

A fourth object of the invention is to provide a surface fastener tape which can be cut into various forms of individual surface fastener pieces for attachment to paper diapers or the like.

A fifth object of the invention is to provide a surface fastener tape which can be stored in stable form until it is cut into individual surface fastener pieces for attachment to paper diapers or the like, facilitating handling.

A sixth object of the invention is to provide a surface fastener tape which can be cut into individual surface fastener pieces for attachment to diapers or the like, each having an adequate degree of elasticity to facilitate using the diaper or the like.

A seventh object of the invention is to provide a method for manufacturing a continuous surface fastener tape, which facilitates stock management and is adapted to be cut into individual surface fastener pieces for use in paper diapers or the like, each having an adhesive layer to facilitate attaching the surface fastener piece to the diaper or the like, in a very simple manner by injection molding using thermoplastic resin.

An eighth object of the invention is to provide a method for manufacturing a continuous length of surface fastener tape, which is adapted to be cut into various kinds of individual surface fastener pieces, in a simple process by specifying the arrangement of male engaging portions on a continuous length of substrate sheet.

A ninth object of the invention is to provide a method for manufacturing a continuous length of surface fastener tape, which is adapted to be cut into individual surface fastener pieces convenient in use in diapers or the like, in a simple process by specifying the shape of the individual surface fastener piece whose substrate sheet has adequate elasticity to facilitate using the diaper or the like.

A tenth object of the invention is to provide a method for manufacturing a continuous length of surface fastener tape, which has a non-woven cloth attached to one flat surface of an engaging-element-free part of a continuous substrate sheet and is hence smooth in touch, in a simple process.

According to a first aspect of the invention, there is provided a surface fastener tape comprising: a continuous length of flat substrate sheet of thermoplastic resin; a male engaging portion molded integrally on part of the substrate sheet; and an adhesive layer formed of an adhesive agent applied to part of the substrate sheet and spaced from the male engaging portion. The surface fastener tape is adapted to be stored in superposed form and to be cut into individual surface fastener pieces.

According to a second aspect of the invention, as an additional feature to that of the first-aspect invention, the male engaging portion and the adhesive layer are arranged on the same surface of the substrate sheet.

According to a third aspect of the invention, as an additional feature to that of the first-aspect invention, the male engaging portion and the adhesive layer are arranged one on each of opposite surfaces of the substrate sheet.

According to a fourth aspect of the invention, as an additional feature to that of the first-, second- or third-aspect invention, the adhesive layer includes a double-sided adhesive tape adhered to part of the substrate sheet.

According to a fifth aspect of the invention, as an additional feature to that of the first-, second-, third- or fourth-aspect invention, male engaging portion is molded centrally and longitudinally on the substrate sheet, and the adhesive layer is a double form composed of two adhesive layers arranged one on each of opposite outer margins of the substrate sheet.

According to a sixth aspect of the invention, as an additional feature to that of the first-, second-, third-, fourth- or fifth-aspect invention, the adhesive layer includes a peel paper attached to an outer surface of the adhesive layer.

According to a seventh aspect of the invention, as an additional feature to that of the first-, second-, third, fourth-, fifth- or sixth-aspect invention, the part of the substrate sheet having the engaging portion and the remaining flat part of the substrate sheet are molded using different kinds of thermoplastic resins in such manner that the remaining flat part is more elastic than the part having the engaging portion.

According to an eighth aspect of the invention, there is provided a method of manufacturing a surface fastener tape, comprising: a first step of continuously supplying thermoplastic resin to a molding machine to mold a continuous length of flat substrate sheet and a male engaging portion, which is composed of a multiplicity of hook-shaped engaging elements projecting from part of the substrate sheet, to form a continuous surface fastener tape, and conveying the continuous surface fastener tape simultaneously with the molding; a second step of applying an adhesive agent to the substrate sheet to form an adhesive layer during the conveying; a third step of storing the continuous surface fastener tape in superposed form; and a fourth step of providing the continuous surface fastener tape with a multiplicity of transverse cutting lines along which the continuous surface fastener tape is to be cut into individual surface fastener pieces.

According to a ninth aspect of the invention, there is alternatively provided a method of manufacturing a surface fastener tape, comprising: a first step of continuously supplying thermoplastic resin to a molding machine to mold a continuous length of flat substrate sheet and a male engaging portion, which is composed of a multiplicity of hook-shaped engaging elements projecting from part of the substrate sheet, to form a continuous surface fastener tape, and conveying the continuous surface fastener tape simultaneously with the molding; a second step of applying an adhesive agent to the substrate sheet to form an adhesive layer during the conveying; a third step of attaching a peel paper to an outer surface of the adhesive layer on the substrate sheet during the conveying; a fourth step of storing the continuous surface fastener tape in superposed form; and a fifth step of providing the continuous surface fastener tape with a multiplicity of transverse cutting lines along which the continuous surface fastener tape is to be cut into individual surface fastener pieces.

According to a tenth aspect of the invention, as an alternative feature, there is provided a method of manufacturing a surface fastener tape, comprising: a first step of continuously supplying thermoplastic resin to a molding machine to mold a continuous length of flat substrate sheet and a male engaging portion, which is composed of a multiplicity of hook-shaped engaging elements projecting from part of the substrate sheet, to form a continuous surface fastener tape, and conveying the continuous surface fastener tape simultaneously with the molding; a second step of attaching a double-sided adhesive tape, which has a pair of adhesive layers formed by applying an adhesive agent onto opposite surfaces, to part of the substrate sheet during the conveying; a third step of storing the continuous surface fastener tape in superposed form; and a fourth step of providing the continuous surface fastener tape with a multiplicity of transverse cutting lines along which the continuous surface fastener tape is to be cut into individual surface fastener pieces.

According to an eleventh aspect of the invention, as another alternative feature, there is provided a method of manufacturing a surface fastener tape, comprising: a first step of continuously supplying thermoplastic resin to a molding machine to mold a continuous length of composite substrate sheet, which is composed of flat sections of the substrate sheet and sections having engaging portions with hook-shaped engaging elements arranged alternately at predetermined distances along the entire length; a second step of applying an adhesive agent to part of each of the flat sections of the composite substrate sheet to form a multiplicity of adhesive layers one for each the flat section; a third step of storing the continuous surface fastener tape in superposed form; and a fourth step of providing the continuous surface fastener tape with a multiplicity of transverse cutting lines along which the continuous surface fastener tape is to be cut into individual surface fastener pieces.

According to a twelfth aspect of the invention, as an additional feature to that of the eighth-, ninth- or tenth-aspect invention, the male engaging portion is molded on the substrate sheet at a position off to one longitudinal side in the first step.

According to a thirteenth aspect of the invention, as an additional feature to that of the eighth-, ninth- or tenth-aspect invention, the male engaging portion is molded centrally on the substrate sheet in the first step, and the adhesive agent is applied to surfaces of opposite longitudinal margins of the substrate sheet to form a pair of adhesive layers one on each side of the substrate sheet in the step, and the substrate sheet is cut into the individual surface fastener pieces in the final step.

According to a fourteenth aspect of the invention, as an additional feature to that of the eighth-, ninth-, tenth-, twelfth- or thirteenth-aspect invention, the part of the substrate sheet having the engaging portion and the remaining flat part of the substrate sheet are molded integrally using different kinds of thermoplastic resins in the first step in such a manner that the remaining flat part of the substrate sheet is more elastic than the part of the substrate sheet having the engaging portion.

According to fifteenth aspect of the invention, as an additional feature of that of the eighth-, ninth-, tenth-, twelfth or thirteenth-aspect invention, in the first step, the part of the substrate sheet having the engaging portion and the part of the substrate sheet having the adhesive layer are molded using the same kind of thermoplastic resin, while the remaining flat part of the substrate sheet between the part having the engaging portion and the part having the adhesive layer is molded using a different kind of thermoplastic resin so as to be more elastic than the part having the engaging portion and the part having the adhesive layer.

According to a sixteenth aspect of the invention, as an additional feature to that of the eighth-, ninth-, tenth-, twelfth- or thirteenth-aspect invention, a non-woven cloth is attached to the part of the substrate sheet on the same surface as the one on which the engaging portion is provided and the non-woven cloth has an adhesive layer confronting the part of the substrate sheet having the adhesive layer.

DETAILED DESCRIPTION OF THE PREFERRED EMBODIMENTS

Various embodiments of a continuous surface fastener tape and a method for manufacturing such continuous surface fastener tape will now be described in detail with reference to the accompanying drawings.

Figure 1:
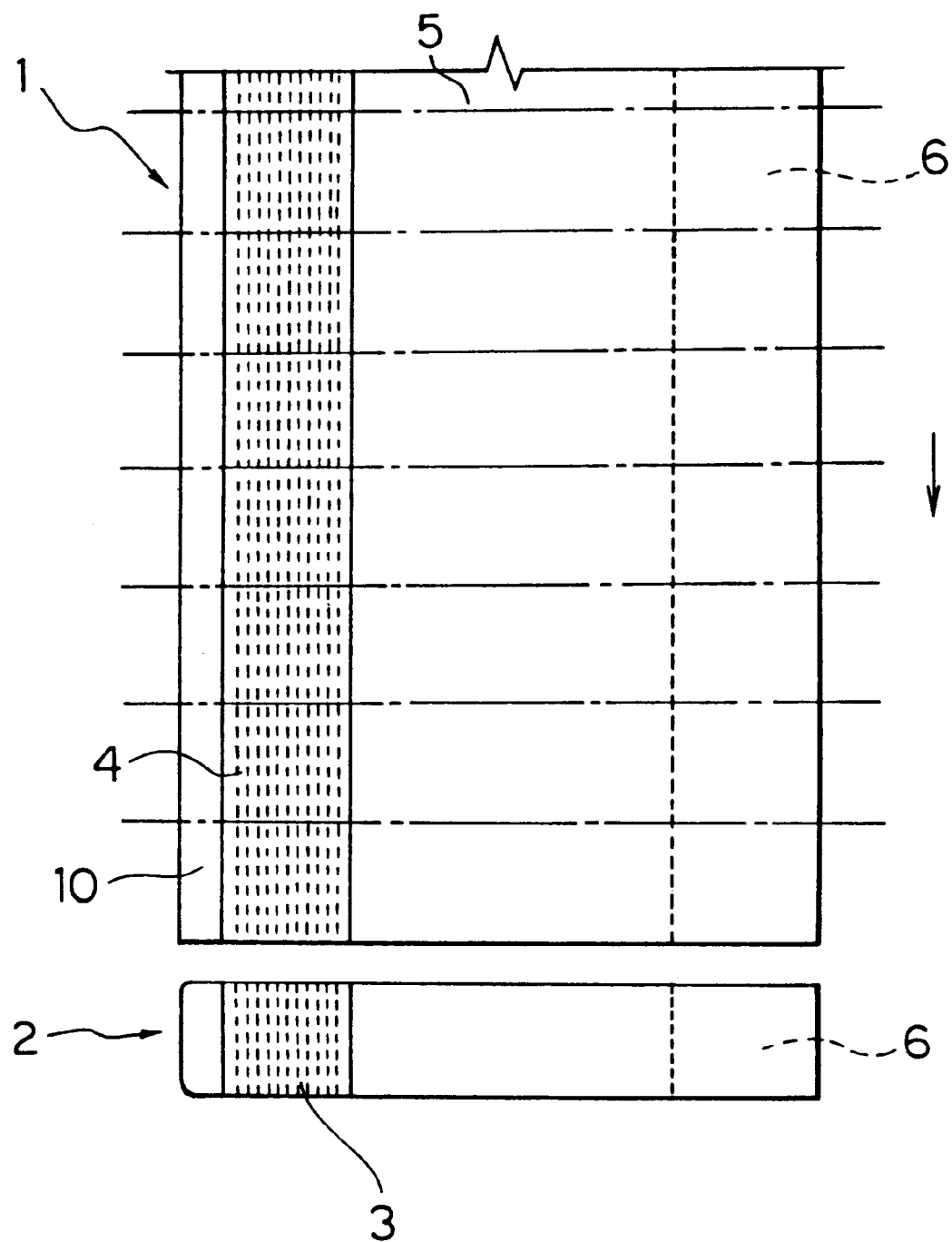
FIG. 1 is a fragmentary plan view of an injection-molded continuous surface fastener tape according to a first embodiment of this invention.
Figure 2:
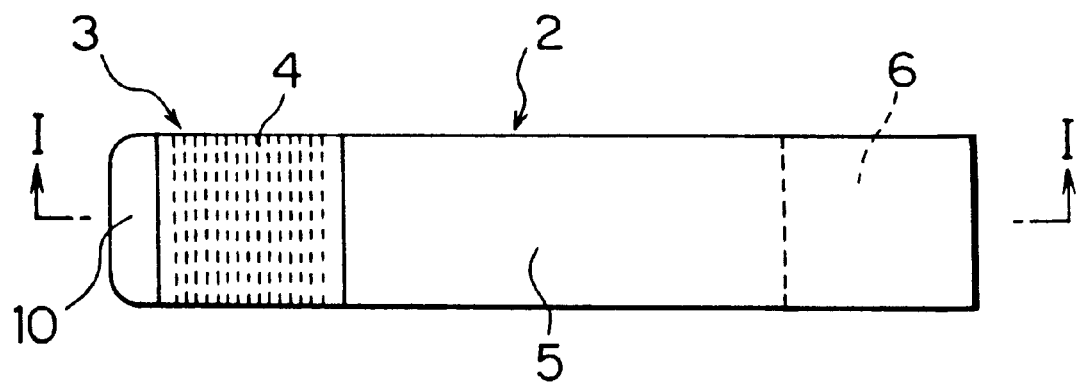
FIG. 2 is a plan view of an individual surface fastener piece cut off the continuous surface fastener tape.
Figure 3:
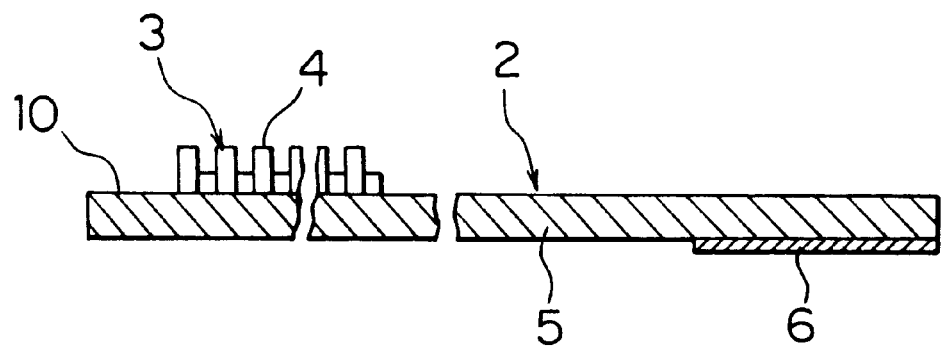
FIG. 3 is a transverse cross-sectional view taken along line I—I of FIG. 2.

FIG. 1 shows a continuous surface fastener tape 1 from which a multiplicity of individual surface fastener pieces 2, each having a male engaging portion (3) and an adhesive layer 6, can be cut for attachment to paper diapers A or other products. The continuous surface fastener tape 1 comprises a continuous length of substrate sheet 5 of thermoplastic resin and a male engaging portion 3, which is composed of a multiplicity of hook-shaped engaging elements 4 standing on a front surface of the substrate sheet 5 and extends along its one longitudinal margin. The substrate sheet 5 and the male engaging portion 3 are simultaneously molded as a unit by injection molding. The molded surface fastener tape 1 has, on a back surface of the substrate sheet 5, the adhesive layer 6 along the other longitudinal margin by applying an adhesive agent, being spaced transversely from the male engaging portion 3 on the front surface. Usually the continuous surface fastener tape 1 is stored as superposed in a roll and may be drawn by some extent and cut along a transverse cutting line to obtain the individual surface fastener pieces 2 of a suitable width for attachment to a diaper or the like.

Further, the surface fastener tape 1 has a uniform-width engaging-element-free flat portion 10 extending along the outer edge of the male engaging portion 3. This flat portion 10 may serve as a grip of the surface fastener piece 2 when the piece 2 is engaged with or disengaged from a companion (female) surface fastener.

The substrate sheet 5 and the male engaging portion 3 of the surface fastener tape 1 are molded by a continuous-type injection molding machine using the same kind of thermoplastic resin, such as polyamide, polyethylene or polypropylene. The adhesive agent applied to the surface of the substrate sheet 5 is preferably an elastomeric adhesive agent exemplified by styrene block copolymers, such as SBS, SIS or SEBS. Epoxy resin or xylene resin may be used for the adhesive agent. Alternatively, the adhesive agent may be applied to and permeated into a piece of cloth or paper, whereupon the adhesive agent is dried to form an adhesive film. In another alternative form, a film devoid of cloth or paper core may be attached to the substrate sheet 5.

Figure 7:
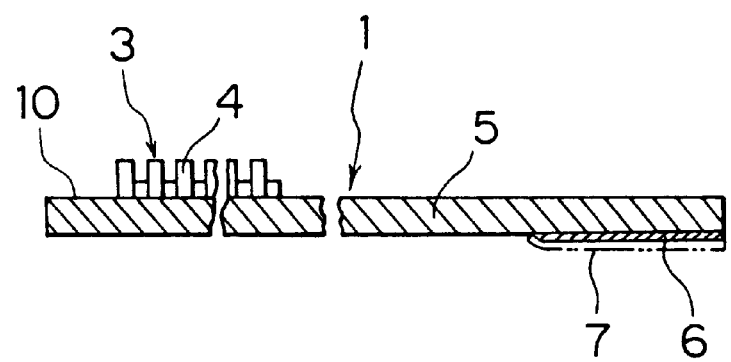
FIG. 7 is a fragmentary transverse cross-sectional view of a continuous surface fastener tape according to a second embodiment of the invention.
Figure 9:
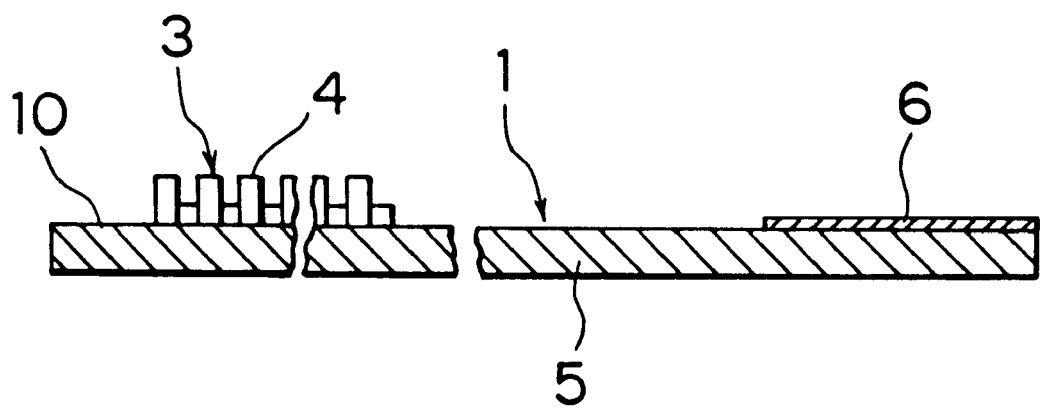
FIG. 9 is a fragmentary transverse cross-sectional view of a continuous surface fastener tape according to a third embodiment of the invention.

FIG. 7 shows a modified surface fastener tape 1 according to a second embodiment, in which a peel paper 7 is attached to the outer surface of an adhesive layer 6, which is arranged on the surface of the substrate sheet 5 along one longitudinal margin, so that the surface fastener tape 1 cannot be attached to a diaper A or the like until the peel paper 7 is removed off. As shown in FIG. 9, on the surface of the substrate sheet 5 where the male engaging portion 3 is provided, the adhesive agent is applied to form the adhesive layer 6 in parallel and opposite to the engaging portion 3. Thus the surface fastener pieces 2 having the engaging portion 3 and the adhesive layer 6 on the same surface can be produced.

Figure 12:
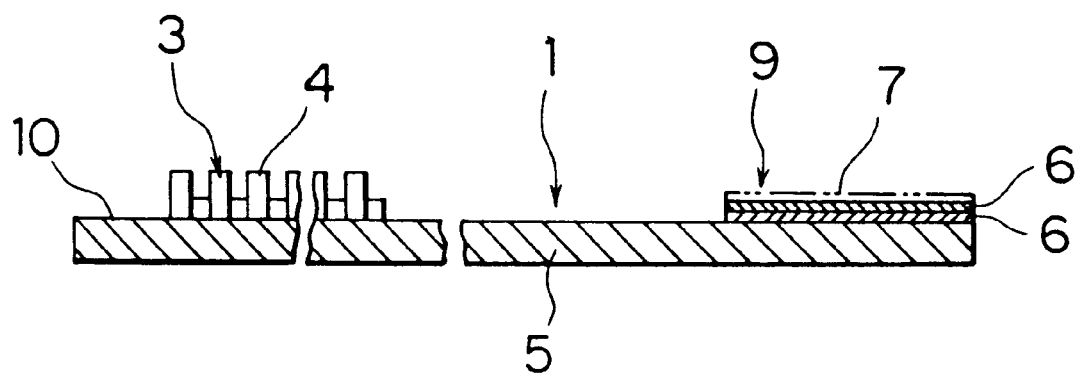
FIG. 12 is a fragmentary transverse cross-sectional view of a continuous surface fastener tape according to a fourth embodiment of the invention.

FIG. 12 shows a further modified surface fastener tape 1 according to a fourth embodiment, in which the engaging portion 3 having engaging elements 4 is integrally molded along the longitudinal edge of the continuous synthetic resin substrate sheet 5 and the adhesive layer 6 is formed by attaching to the substrate sheet 5 a commercially available double-sided adhesive tape 9 carrying adhesive agent on opposite surfaces.

Figure 15:
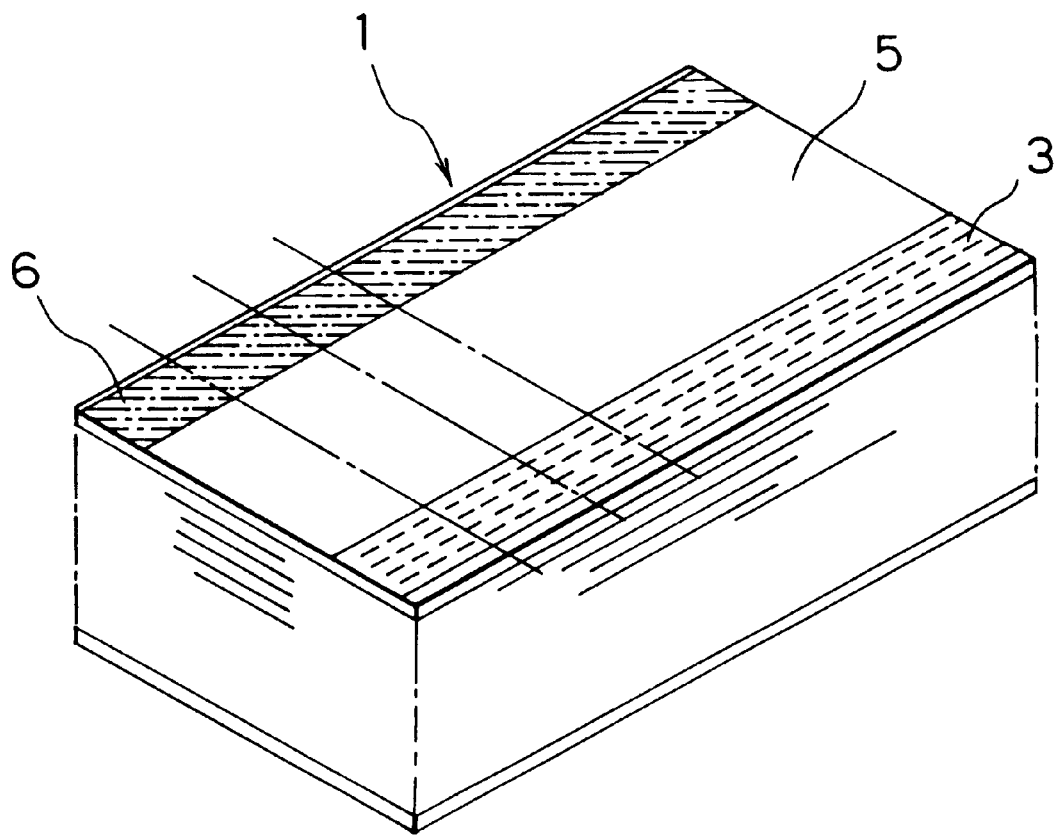
FIG. 15 is a perspective view of a stack of surface fastener tapes.

For alternative stock management, the continuous surface fastener tape 1 may be stored in stack as shown in FIG. 15. The continuous surface fastener tape 1, in which the male engaging portion 3 and the adhesive layer 6 are arranged on the same surface of a continuous-length substrate sheet 5, is cut into a predetermined intermediate length, and then these intermediate-length surface fastener tapes 1 are piled in stack for storage. When the surface fastener tape 1 is used for the diaper A or the like, this stack of the intermediate-length surface fastener tapes 1 is cut into individual surface fastener pieces 2 of a predetermined final length (width) for attachment to paper diapers A during the paper diaper production.

Figure 16:
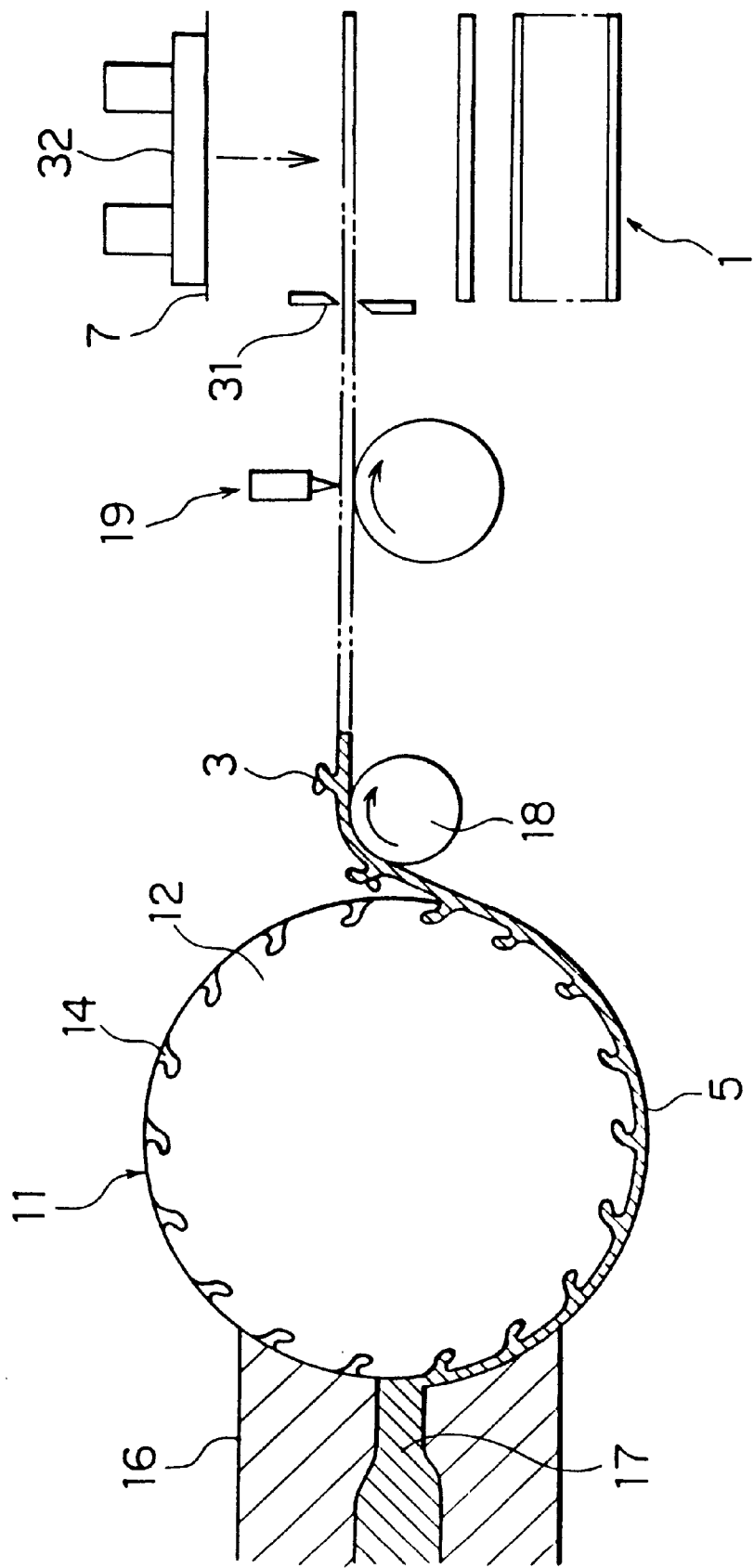
FIG. 16 is a fragmentary vertical cross-sectional view of an apparatus for manufacturing the stack-type surface fastener tapes of FIG. 15.

Specifically, the male engaging portion 3 is molded on one surface of the substrate sheet 5 using a continuous-type injection molding machine 11 of FIG. 16, and adhesive agent is applied to the same surface of the substrate sheet 5 by an adhesive agent applicator 19 to form the adhesive layer 6, whereupon the resulting continuous surface fastener tape 1 is cut at a predetermined length successively by a cutter 31 and then piled in stack. When the number of the cut surface fastener tapes 1 reaches a predetermined value, the peel paper 7 is pressed against the top of the stack by a peel paper attaching device 30 and is thereby attached to the front surface of the uppermost surface fastener tape 1, so that the cut surface fastener tapes 1 are placed over in stack for storage.

Figure 14:
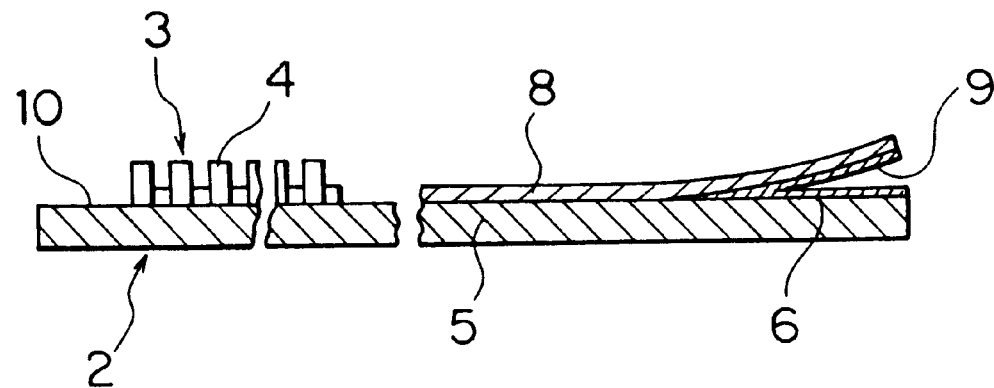
FIG. 14 is a fragmentary transverse cross-sectional view of a continuous surface fastener tape according to a fifth embodiment of the invention.

FIG. 14 shows a still further modified continuous surface fastener tape 1 according to a fifth embodiment (described below).

Figure 17:
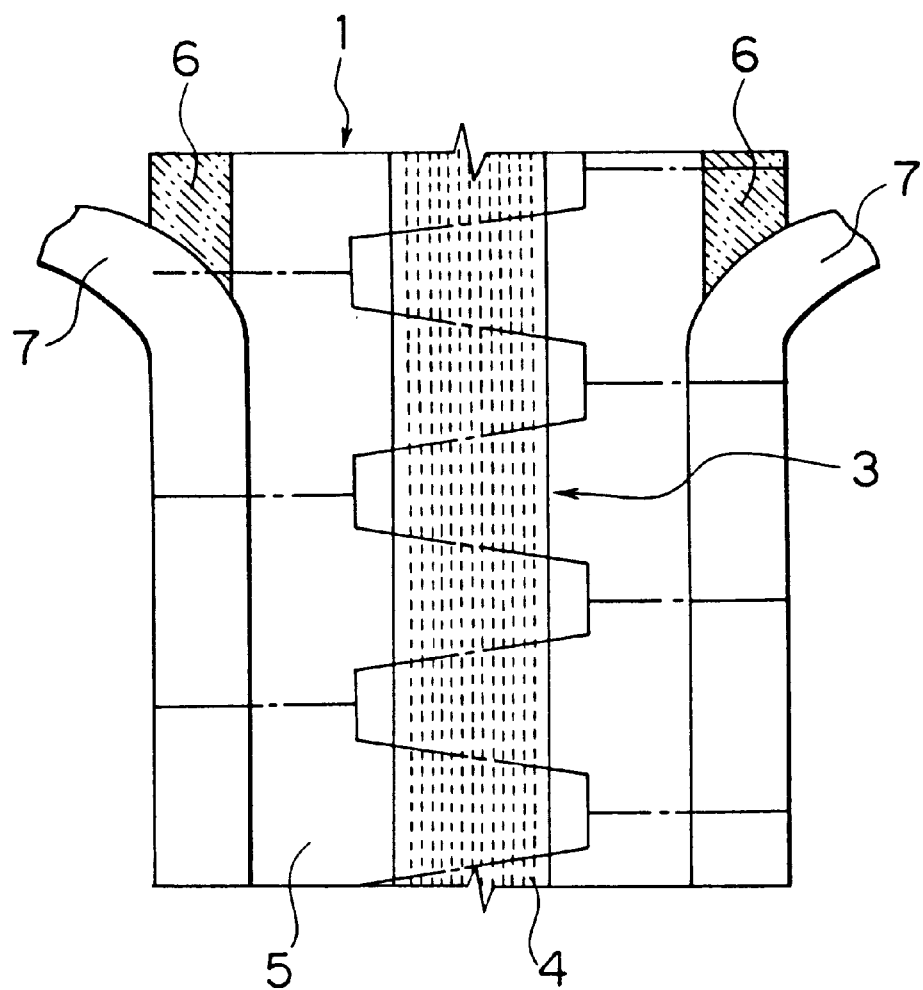
FIG. 17 is a fragmentary plan view of a continuous surface fastener ta according to a sixth embodiment of the invention.
Figure 18:
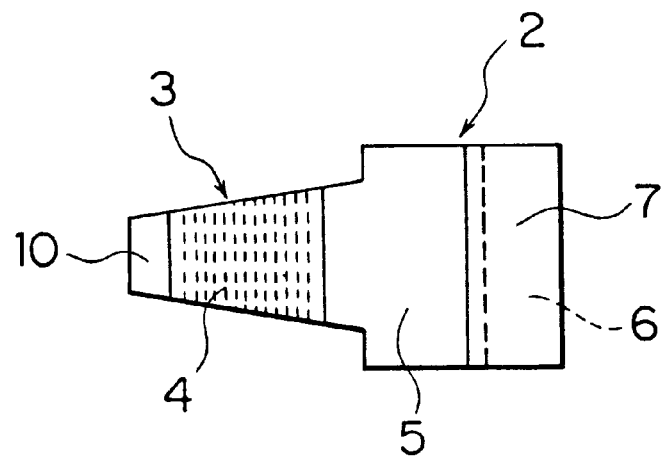
FIG. 18 is a plan view of an individual surface fastener piece cut off the continuous surface fastener tape of the sixth embodiment.

FIG. 17 shows an additional modified continuous surface fastener tape 1 according to a sixth embodiment, in which a male engaging portion 3 is composed of a multiplicity of hook-shaped engaging elements 4 standing on the front surface of a continuous-length substrate sheet 5 and arranged within a suitable width of central and longitudinal range. And a pair of adhesive layers 6 are formed by applying adhesive agent to the front surface of the substrate sheet 5 within a pair of longitudinal margins extending parallel to the male engaging portion 3. The outer surface of each adhesive layer 6 is covered by a peel paper 7. In use, the continuous surface fastener tape 1 is cut along cutting lines (dash-and-dot lines) to provide individual surface fastener pieces 2 of FIG. 18. In each surface fastener piece 2, the length of the male engaging portion 3 is substantially a half of that of the adhesive layer 6 so that a large attaching area with respect to the diaper A can be achieved. Assuming that the surface fastener tape 1 is cut along parallel transverse cutting lines through the entire width, each of the individual surface fastener pieces 2 has two adhesive layers 6, each covered with the peel paper 7, and one male engaging portion 3, which are common in length. In use, with only one peel paper 7 removed off the corresponding adhesive layer 6, the surface fastener piece 2 is attached to the diaper A. In disposing the used diaper A, if the other peel paper 7 is removed off the corresponding adhesive layer 6, which can serve to tighten up the diaper A. Alternatively the peel papers 7 for covering the adhesive layers 6 may be omitted.

Figure 20:
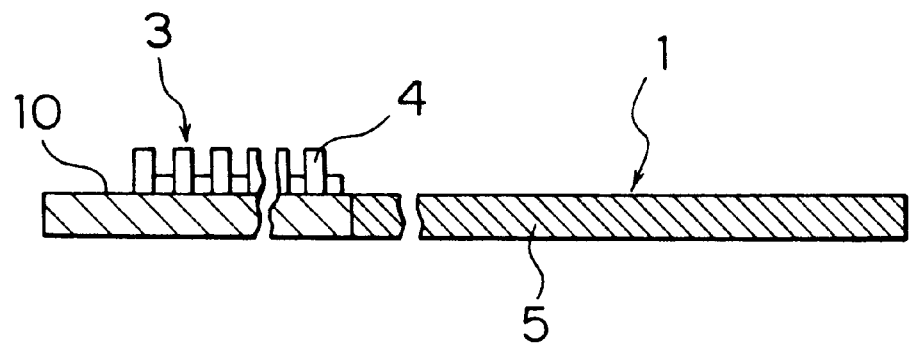
FIG. 20 is a fragmentary transverse cross-sectional view of a continuous surface fastener tape according to a seventh embodiment of the invention.
Figure 22:
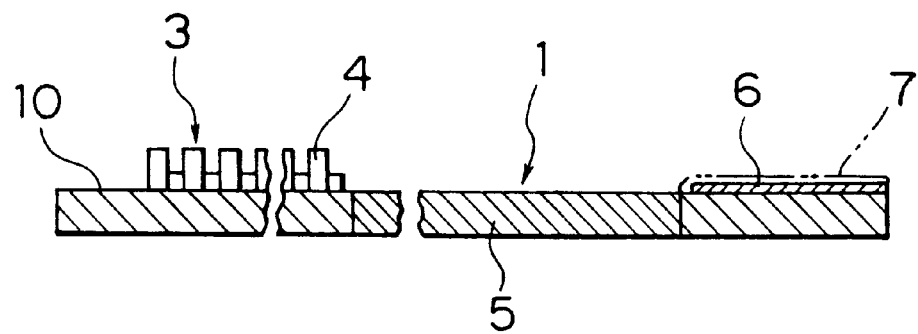
FIG. 22 is a fragmentary transverse cross-sectional view of a continuous surface fastener tape according to an eighth embodiment of the invention.

FIG. 20 shows still another modified continuous surface fastener tape 1 according to a seventh embodiment, in which the part having the engaging portion 3 and the remaining flat part of a continuous-length substrate sheet 5 are molded using different kinds of thermoplastic resins in such a manner that the flat part is adequately elastic so that the surface fastener piece 2 is adequately expandable/contractible. Alternatively, as shown in FIG. 22, according to an eighth embodiment, in which the part having the engaging portion 3 and the part having the adhesive layer 6 in the flat part of the continuous-length substrate sheet 5 are molded of the same kind of thermoplastic resin, while the remaining intermediate part of the substrate sheet 5 between the engaging portion 3 and the adhesive layer 6 is molded of a different kind of thermoplastic resin. Thus the intermediate part is more elastic than the engaging-element-existing part and the adhesive-layer-existing part.

In the surface fastener tape 1, the non-elastic part such as the part having the engaging portion 3 may be molded of polyamide, and the elastic part may be molded of polyethylene or a suitable combination of thermoplastic resins, such as polypropylene and polyethylene.

Figure 24:
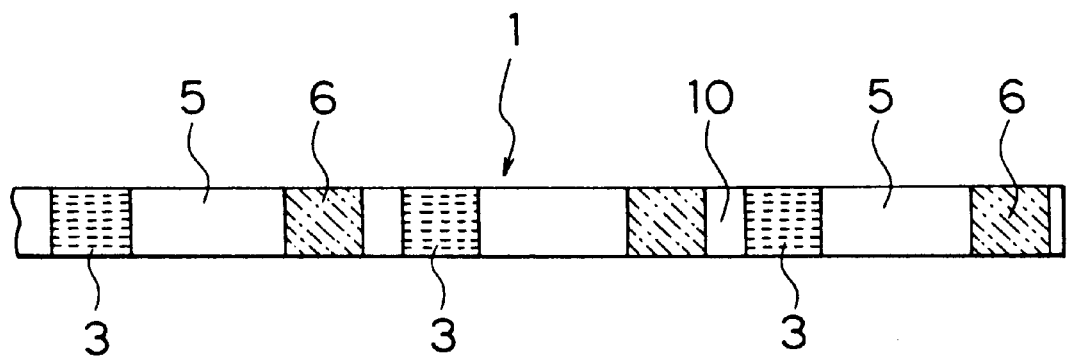
FIG. 24 is a fragmentary plan view of a continuous surface fastener tape according to a ninth embodiment of the invention.

FIG. 24 shows a still further modified continuous surface fastener tape 1 according to a ninth embodiment, in which successive male engaging portions 3 having engaging elements 4 are arranged on the front surface of a continuous-length substrate sheet 5 of thermoplastic resin at regular distances along its entire length. And successive adhesive layers 6 are arranged on the front surface of the substrate sheet 5 at regular distances longitudinally in such a manner that each adhesive layer 6 is disposed adjacent to the respective preceding male engaging portion 3 and is spaced from the former engaging portion 3 it by a predetermined gap. In use, the continuous surface fastener tape 1 is cut transversely between the male engaging portion 3 and the adjacent adhesive layer 6 to provide an individual surface fastener piece 2 for attachment to the diaper A or the like.

In the surface fastener tape 1 of the fifth embodiment of FIG. 14, a male engaging portion 3 is molded on the front surface of a continuous-length substrate sheet 5 of thermoplastic resin, having engaging elements 4 along one longitudinal margin, and an adhesive layer 6 is formed on the front surface of the substrate sheet 5 along the other longitudinal margin. And a non-woven cloth 8 is attached to the front surface of the substrate sheet 5 to cover the adhesive layer 6 and the engaging-element-existing part of the substrate sheet 5. Another adhesive layer 6 is formed on the inner surface of the non-woven cloth 8 in confronting relation to the adhesive layer 6 on the substrate sheet 5. The non-woven cloth 8 serves as a peel paper; in use, the tab of the diaper A may be sandwiched between the confronting adhesive layers 6, 6 of the individual surface fastener piece 2 as the non-woven cloth 8 is partly peeled. The substrate-sheet-side adhesive layer 6 and the non-woven-cloth-side adhesive layer 6 may be different in adhering strength of adhesive agent so that the two adhesive layers 6, 6 can be separated easily when the surface fastener piece 2 is to be attached to the diaper A.

Figure 5:
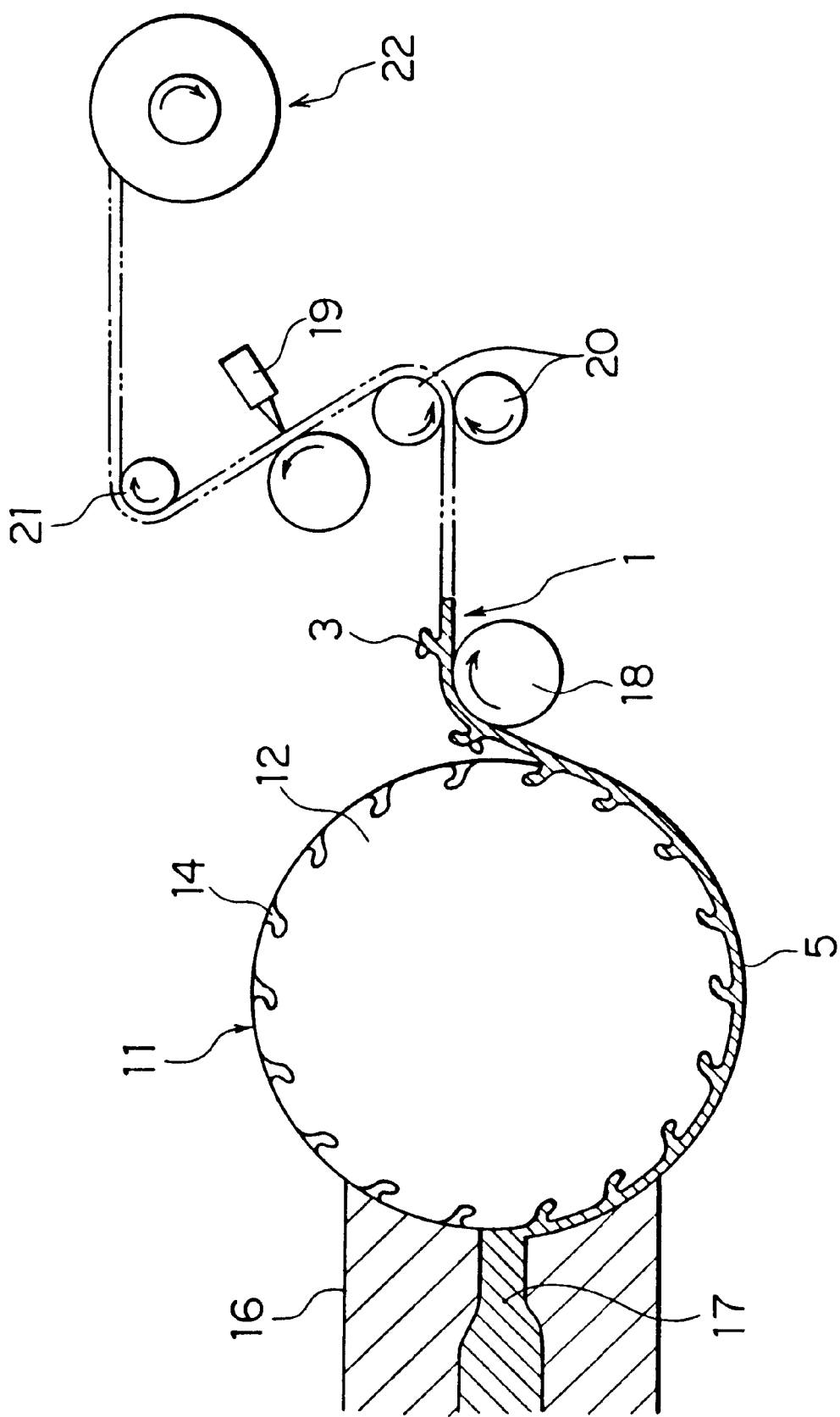
FIG. 5 is a fragmentary vertical cross-sectional view of an injection molding machine for molding the continuous surface fastener tape of the first embodiment.
Figure 6:
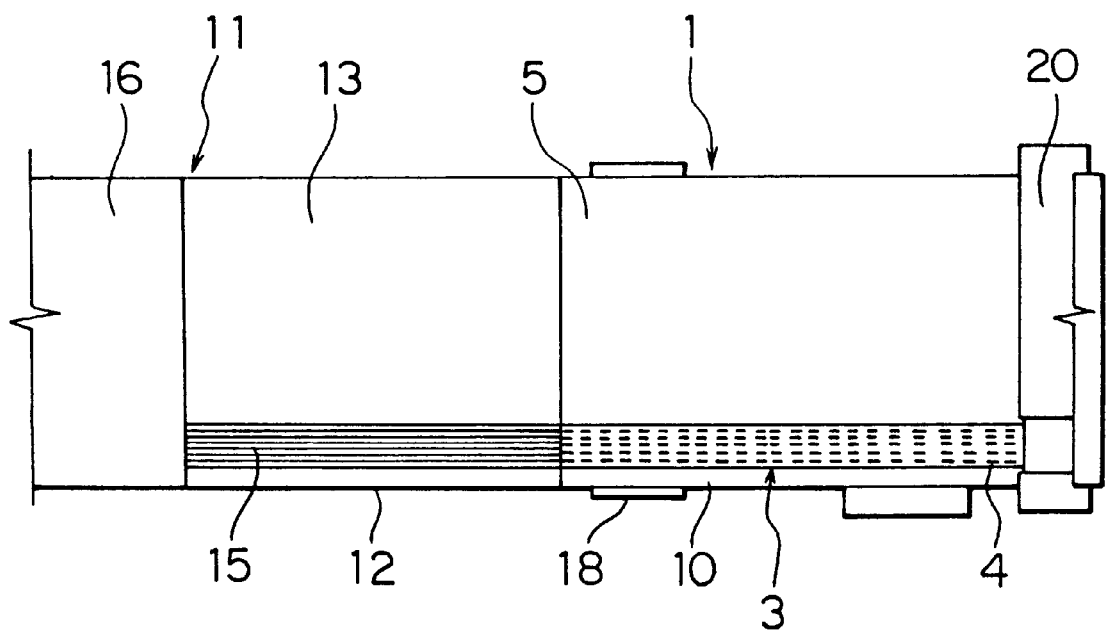
FIG. 6 is a fragmentary plan view of the injection molding machine.

The surface fastener tape 1 is manufactured in the following manner using the continuous-type injection molding machine 11 of FIGS. 5 and 6. In the injection molding machine 11, a die wheel 12 has in its circumferential surface a substrate-sheet-forming shallow recess 13 and an engaging-portion-forming section 15 composed of a multiplicity of hook-shaped cavities 14. An injection nozzle 16 is disposed in confronting relation to the circumferential surface of the die wheel 12 and having a sprue 17 through which molten resin is to be injected to the die wheel 12. A guide roller 18 is disposed near the die wheel 12 and diametrically opposite to the injection nozzle 16 with respect to the die wheel 12, and downstream of the guide roller 18, a pair of drawing/turning rollers 20 are disposed. A turning roller 21 is disposed upwardly of the drawing/turning rollers 20. The adhesive agent applicator 19 is disposed between the drawing/turning rollers 20 and the turning roller 21. Downstream of the turning roller 21, a take-up roller 22 is disposed.

In the first step of the surface fastener tape manufacturing method, the molten resin is injected to the circumferential surface of the die wheel 12 from the injection nozzle 16 via the sprue 17 to continuously mold a surface fastener tape 1, during which time a flat substrate sheet 5 and a male engaging portion 3 are simultaneously molded. The male engaging portion 3 is composed of a multiplicity of hook-shaped engaging elements 4 standing on the substrate sheet 5 and extends longitudinally along the entire length of the substrate sheet 5. The molded continuous surface fastener tape 1 is removed off the die wheel 12 horizontally by the guide roller 18.

Figure 4:
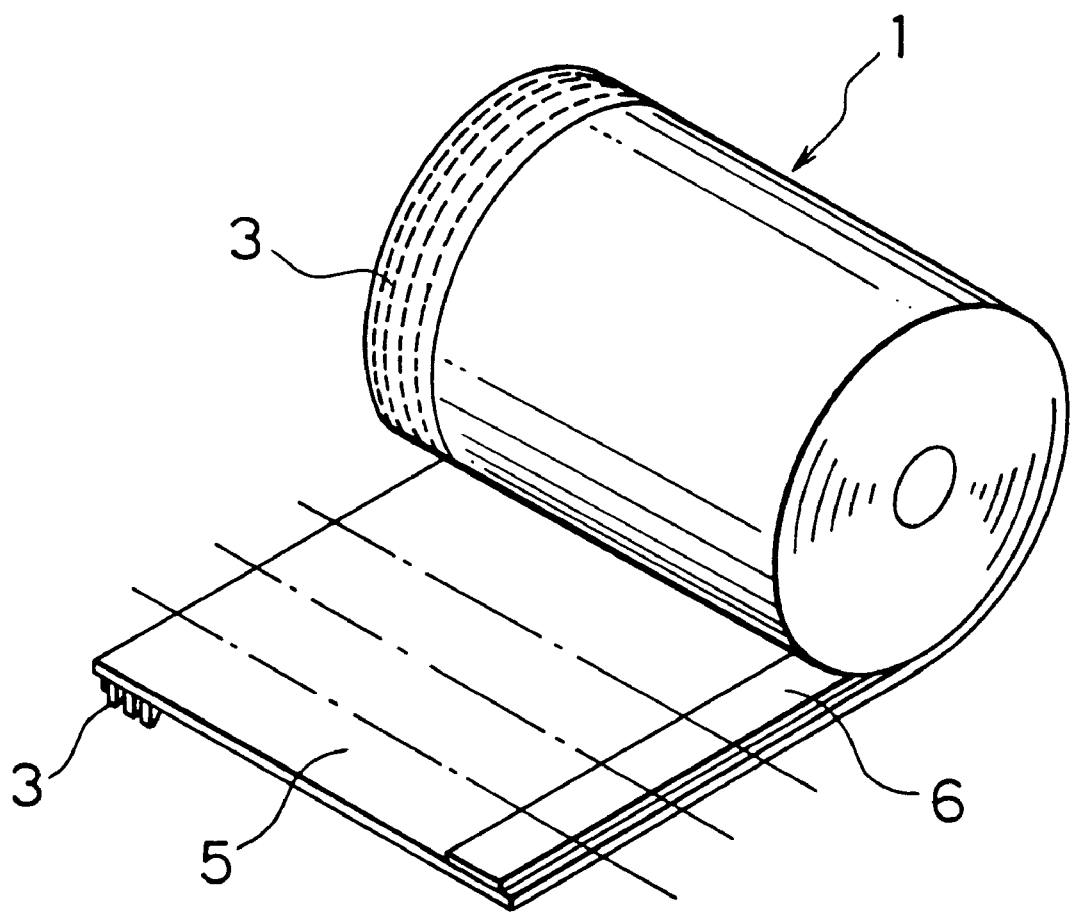
FIG. 4 is a perspective view of a roll of the continuous surface fastener tape.

In the second step, the direction of traveling of the surface fastener tape 1 is turned from horizontal to upward by the drawing/turning rollers 20. While the surface fastener tape 1 travels upwardly, adhesive agent is applied to the side opposite to the engaging portion 3, namely the back surface of the substrate sheet 5 to form an adhesive layer 6 in and along a longitudinal range, which is spaced from the engaging element portion 3, by the adhesive agent applicator 19. In the third step, the surface fastener tape 1 is wound by the take-up roller 22, which is disposed downstream of the turning roller 21, and is thus stored in superposed form, i.e., in roll as shown in FIG. 4. Finally the surface fastener tape 1 is cut into individual surface fastener pieces 2 of a predetermined length for attachment to the diapers A during the diaper production.

Figure 8:
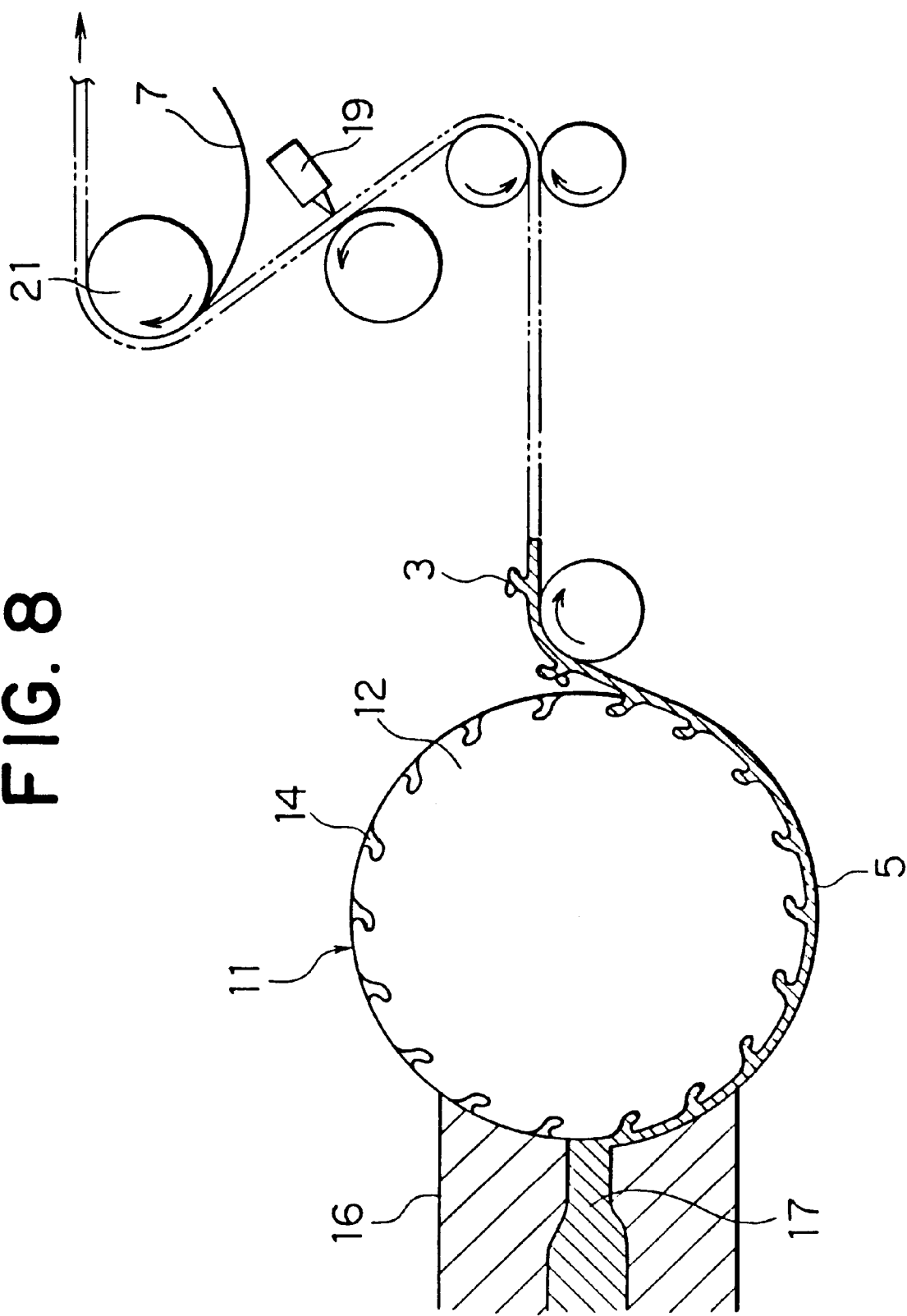
FIG. 8 is a fragmentary vertical cross-sectional view of an injection molding machine for molding the continuous surface fastener tape of the second embodiment.

In the manufacturing method for the surface fastener tape 1 of FIG. 7 having the peel paper 7 attached on the adhesive layer 6 disposed along one side of the substrate sheet 5, the male engaging portion 3 is molded on one surface of the substrate sheet 5 by the same continuous-type injection molding machine 11 as that of the previous embodiment as shown in FIG. 8, and adhesive agent is applied to the other surface of the substrate sheet 5 by the adhesive agent applicator 19 to form the adhesive layer 6. Then the peel paper 7 is supplied to the turning roller 21, which is disposed downstream of the adhesive agent applicator 19, and is attached to the surface of the adhesive layer 6, whereupon the resulting surface fastener tape 1 is conveyed for storage in a suitable superposed form.

Figure 10:
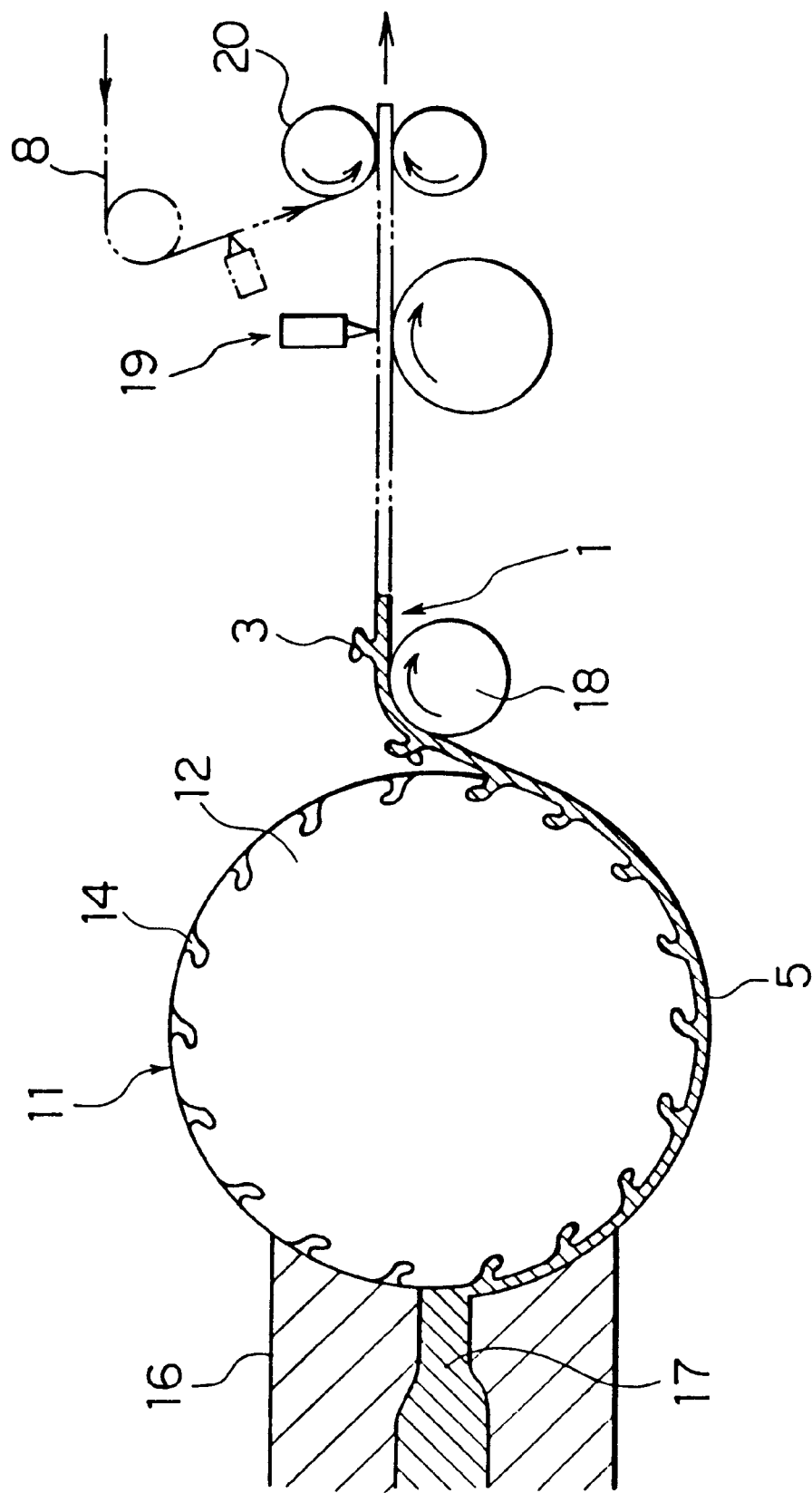
FIG. 10 is a fragmentary vertical cross-sectional view of an injection molding machine for molding the continuous surface fastener tape of the third embodiment.
Figure 11:
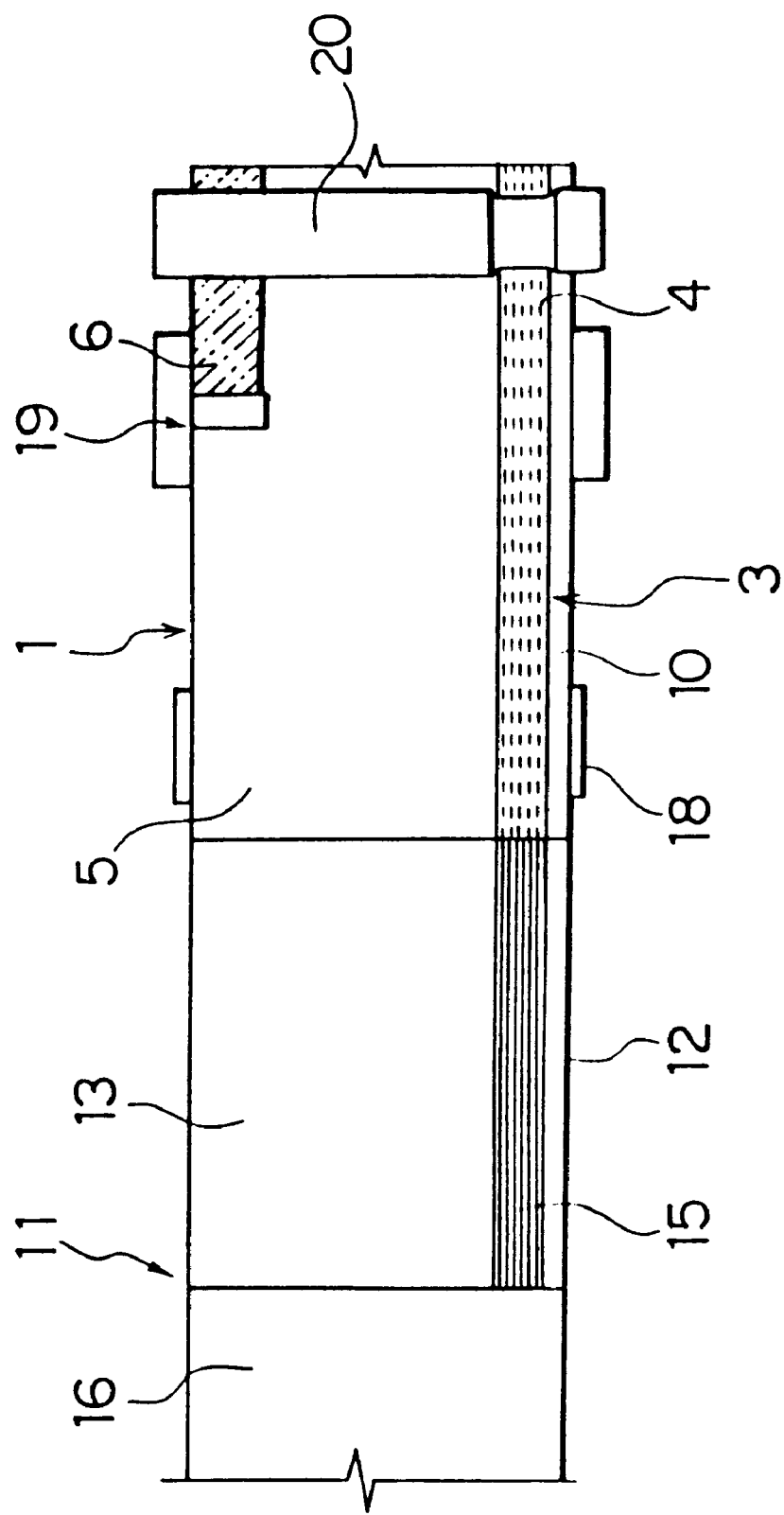
FIG. 11 is a fragmentary plan view of the injection molding machine of FIG. 10.

In the manufacturing method for the surface fastener tape 1 of FIG. 9, in which the male engaging portion 3 and the adhesive layer 6 are molded on the same surface of the substrate 5 along one longitudinal margin, the surface fastener tape 1 is molded by a continuous-type injection molding machine 11 of FIGS. 10 and 11, and adhesive agent is applied to the front surface of the substrate sheet 5 along the other longitudinal margin, which is spaced from the male engaging portion 3, by an adhesive agent applicator 19 disposed at the other longitudinal margin between a guide roller 18 and a pair of drawing rollers 20. Thus the adhesive layer 6 is formed as shown in FIG. 11, whereupon the resulting surface fastener tape 1 is drawn and conveyed by the drawing rollers 20 for storage in a suitable superposed form.

Figure 13:
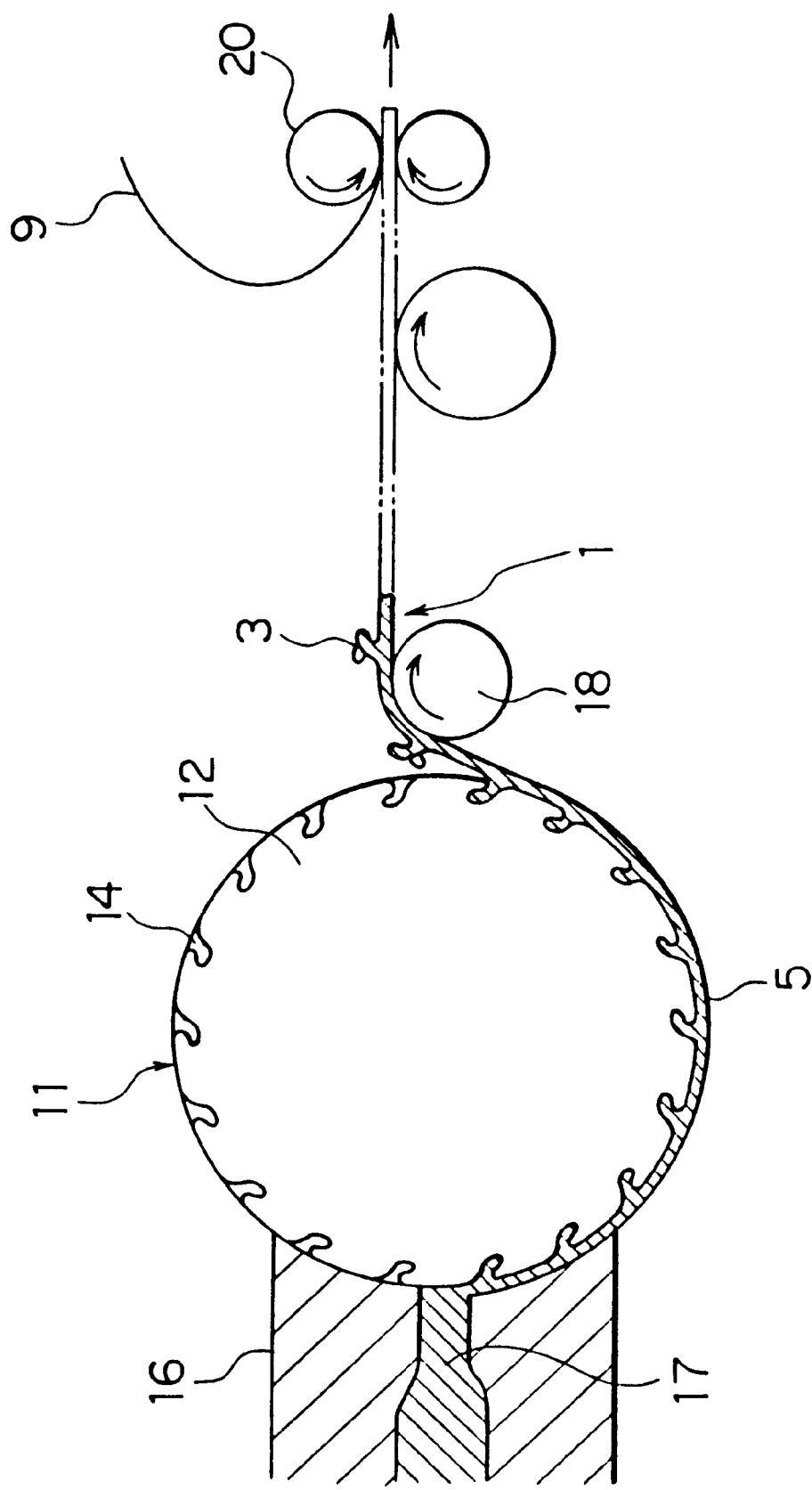
FIG. 13 is a fragmentary vertical cross-sectional view of an injection molding machine for molding the continuous surface fastener tape of the fourth embodiment.

In the manufacturing method for the surface fastener tape 1 of FIG. 12, in which the male engaging portion 3 and the adhesive layer 6 are formed on the front surface of the substrate sheet 5, and a double-sided adhesive tape 9 is attached as the adhesive layer 6, a continuous-type injection molding machine 11 of FIG. 13 is used. The double-sided adhesive tape 9 is supplied to a pair of drawing rollers 20 and is attached to the surface of the substrate sheet 5. Then the resulting surface fastener tape 1 is conveyed for storage in a suitable superposed form.

In the manufacturing method for the surface fastener tape 1 of FIG. 14, in which a non-woven cloth 8 is attached, the non-woven cloth 8 using synthetic fibers, such as of polyamide or polyester, is cut into a size to conform to the substrate-sheet-forming shallow recess 13 (FIG. 11) of the die wheel 12 and is supplied to the pair of drawing rollers 20 as shown by phantom line in FIG. 10, with an adhesive layer 6 formed along one longitudinal margin to confront the adhesive layer 6 on the substrate sheet 5, substantially in the same manner of the previous embodiment using the continuous-type injection molding machine 11. At that time, the upper drawing roller 20 is a stepped roller so that the adhesive layers 6, 6 can pass smoothly through the drawing rollers 20. The drawing rollers 20 have heating and pressing function so that the non-woven cloth 8 is attached to the front surface of the engaging-element-free part of the substrate sheet 5 while the surface fastener tape 1 and the non-woven cloth 8 pass through the drawing rollers 20. The resulting surface fastener tape 1 is then discharged out of the injection molding machine for storage in a suitable superposed form.

Figure 19:
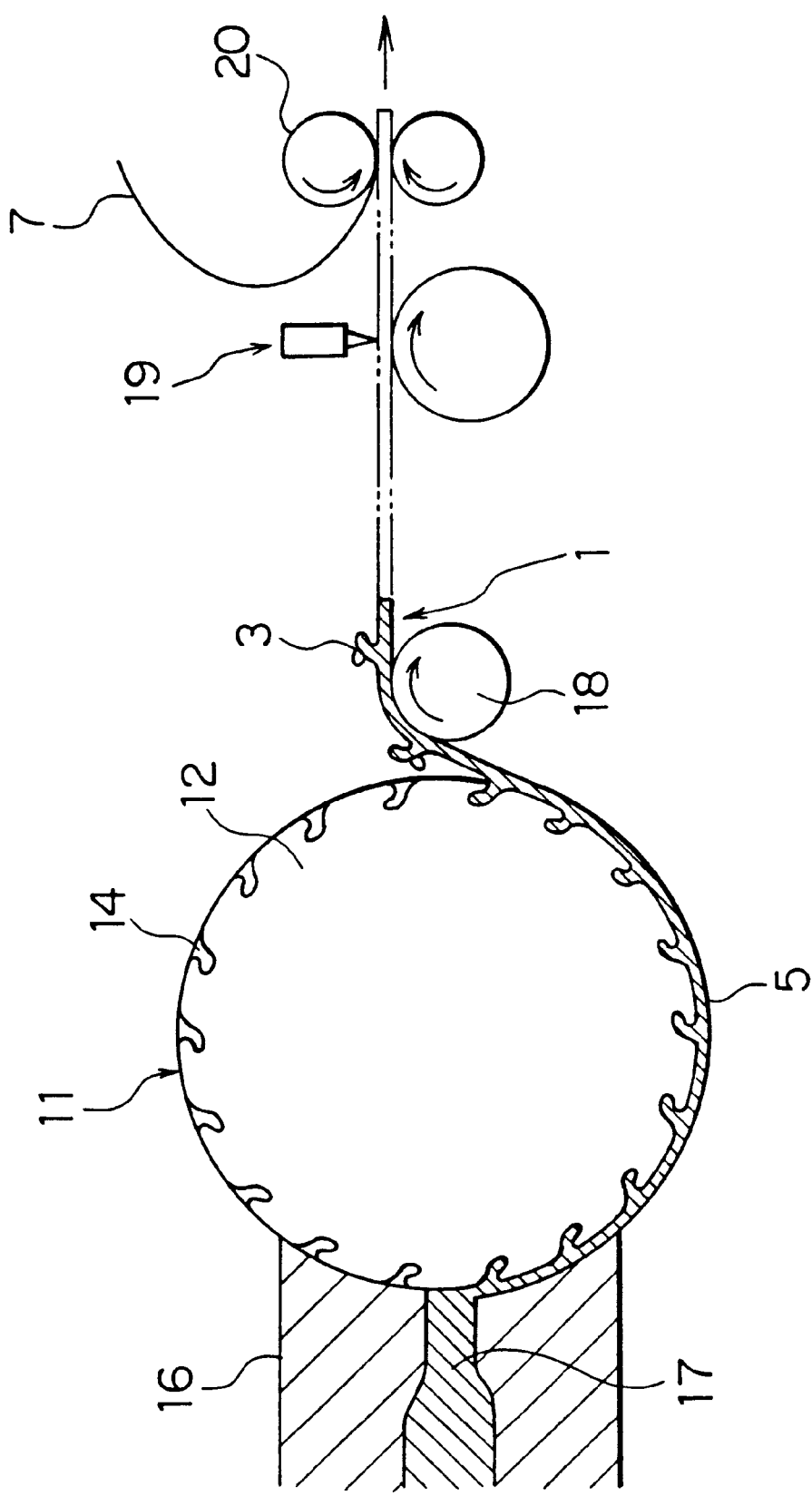
FIG. 19 is a fragmentary vertical cross-sectional view of an injection molding machine for molding the continuous surface fastener tape of the sixth embodiment.

In the manufacturing method for the surface fastener tape 1 of FIG. 17, the continuous injection-molding machine is used with which the male engaging portion 3 is molded centrally on the continuous-length substrate sheet 5 using the die wheel 12 (FIG. 19) having a multiplicity of engaging-element-forming cavities 14 centrally in the circumferential surface, and the adhesive layers 6, 6 are formed on and along opposite longitudinal margins of the substrate sheet 5 by a pair of laterally spaced adhesive agent applicators 19. And a pair of peel papers 7, 7 are attached to the corresponding adhesive layers 6, 6 by the drawing rollers 20, 20. The surface fastener tape 1 is manufactured in substantially the same process as the embodiment of FIG. 10.

Figure 21:
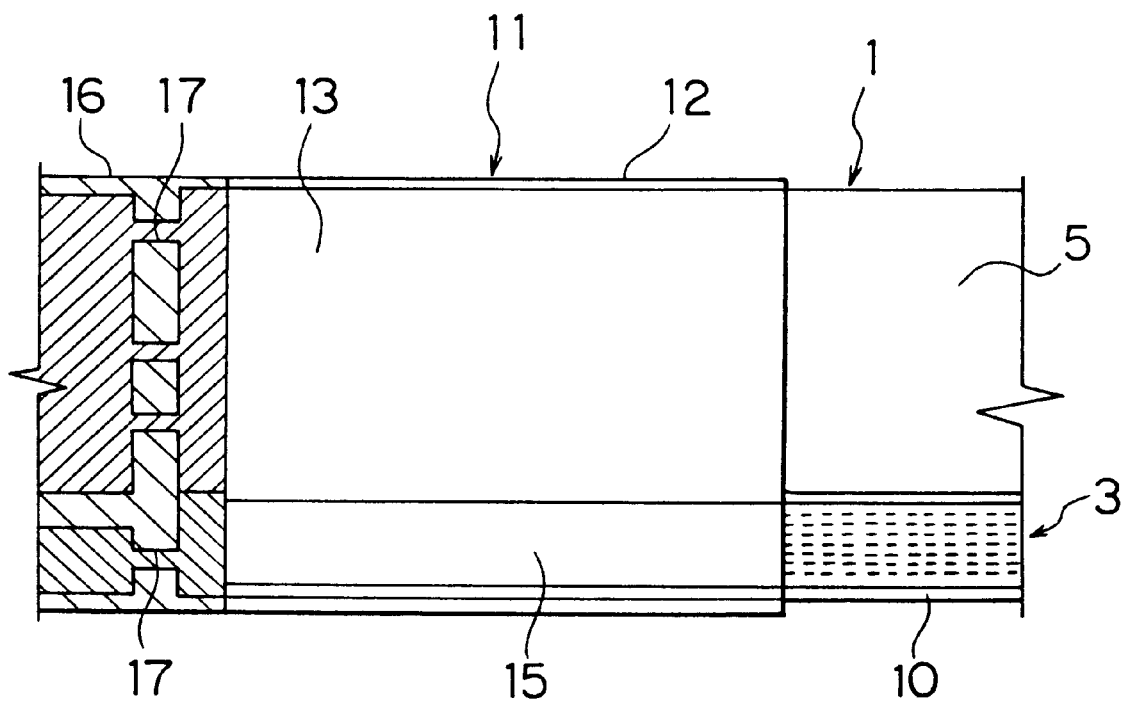
FIG. 21 is a fragmentary plan view of an injection molding machine for molding the continuous surface fastener tape of the seventh embodiment.

For molding the part having the engaging portion 3 and the flat part of the continuous substrate sheet 5 of FIG. 20 using different kinds of thermoplastic resins, two injection nozzles 16, 16 inject molten thermoplastic resins of different kinds, e.g. polyethylene and polyamide, to the substrate-sheet-forming shallow recess 13 and the engaging-element-forming section 15, respectively, of a die wheel 12 of FIG. 21 from the corresponding sprues 17, 17. This manufacturing process is substantially identical with that of the foregoing embodiments.

Figure 23:
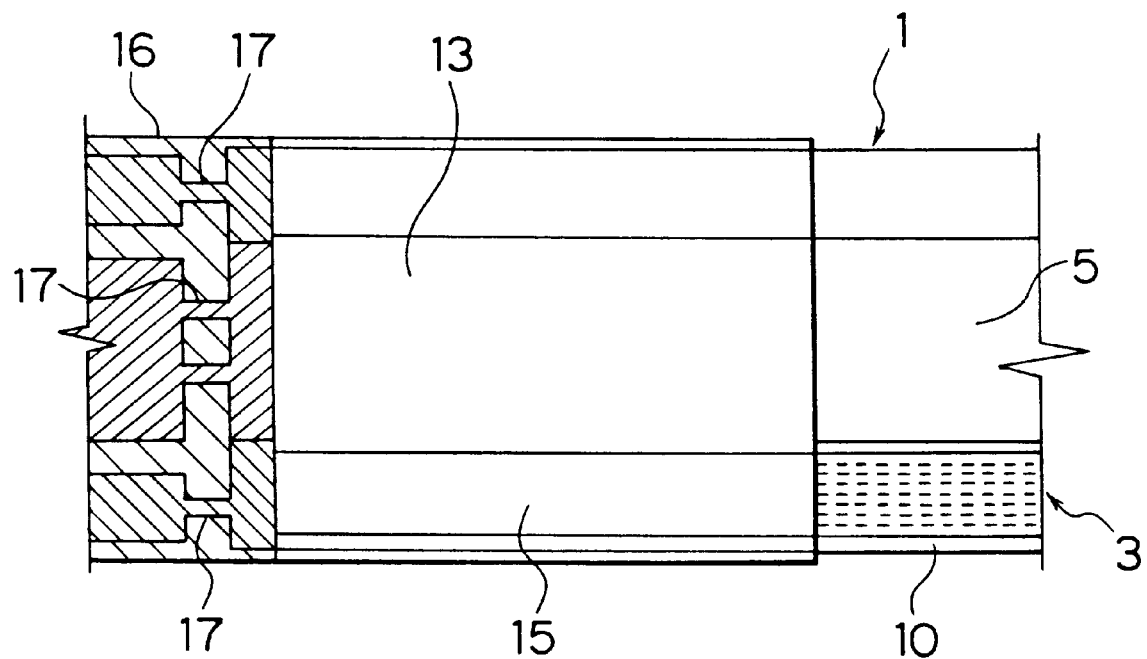
FIG. 23 is a fragmentary plan view of an injection molding machine for molding the continuous surface fastener tape of the eighth embodiment.

The manufacturing method for the surface fastener tape 1 of FIG. 22, in which the part having the engaging portion 3 and the part having the adhesive layer 6 of the substrate sheet 5 are molded using the same kind of thermoplastic resin while the flat part between the engaging-element-existing part and the adhesive-layer-existing part is molded using a different kind of thermoplastic resin, is identical with the previous embodiment except that a central injection nozzle 16 is used independently of two side injection nozzles 16, 16 as shown in FIG. 23. And the surface fastener tape 1 is manufactured by the same process as the foregoing embodiment.

Figure 25:
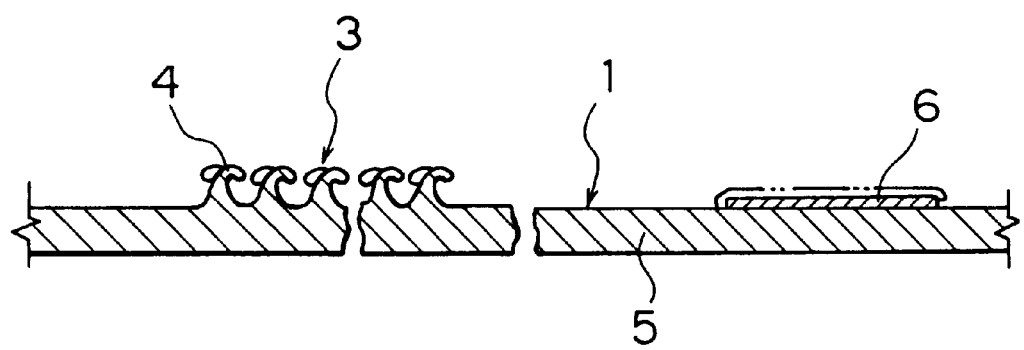
FIG. 25 is a longitudinal cross-sectional view of the continuous surface fastener tape of the ninth embodiment.
Figure 26:
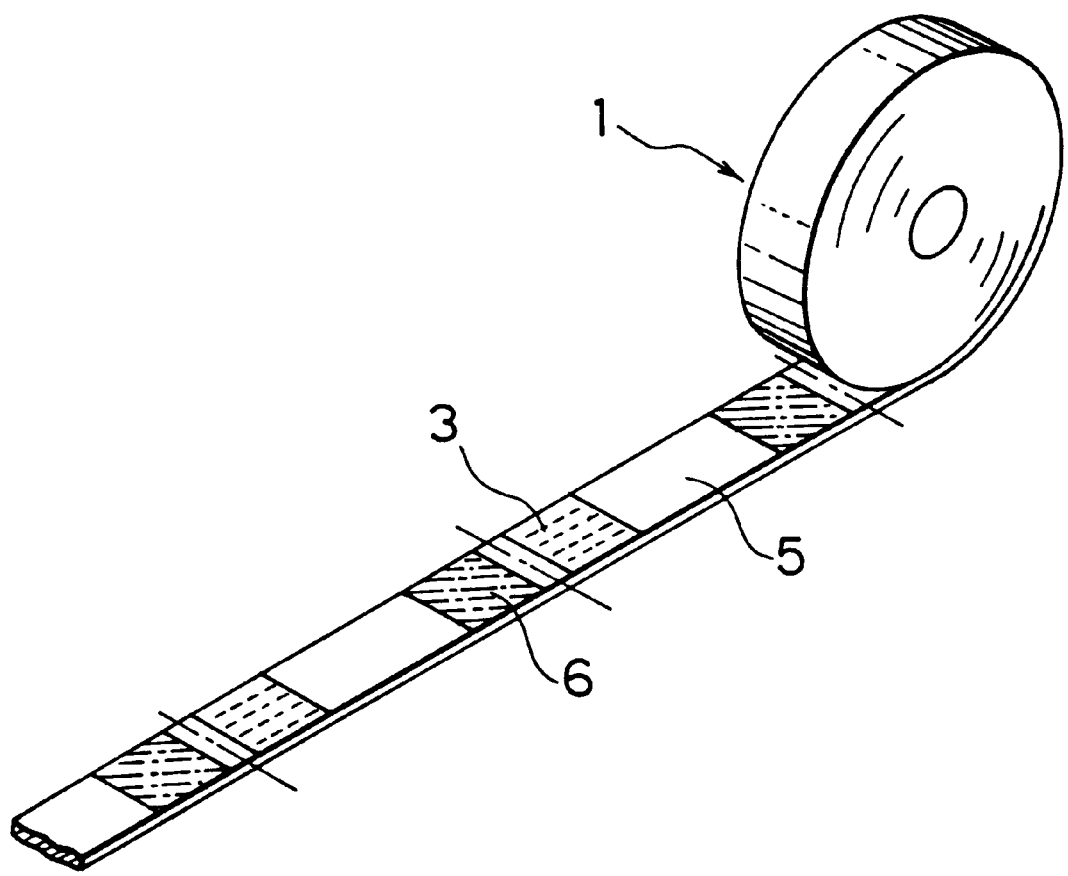
FIG. 26 is a perspective view of a roll of the continuous surface fastener tape of the ninth embodiment.
Figure 27:
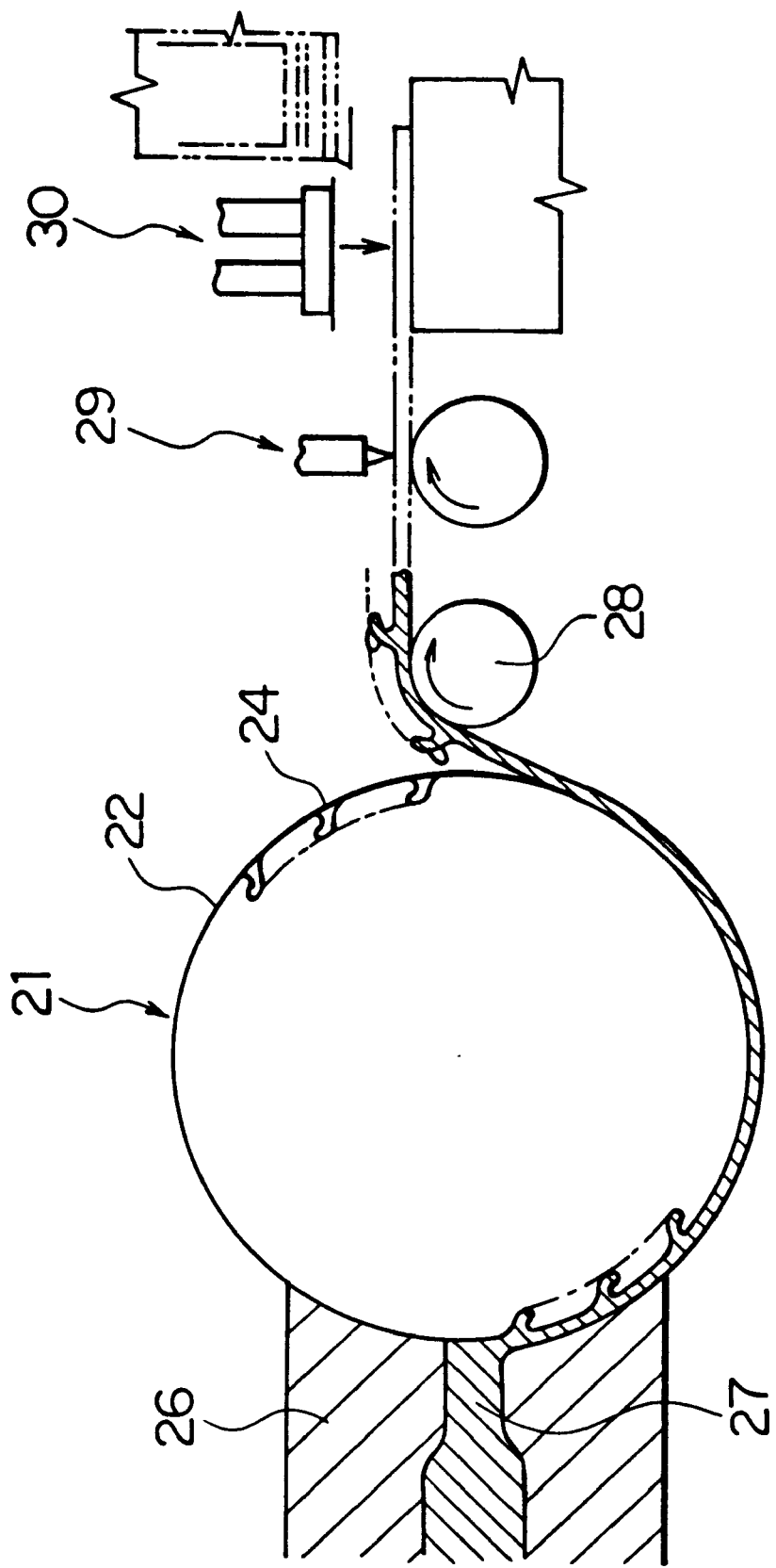
FIG. 27 is a fragmentary vertical cross-sectional view of an injection molding machine for molding the continuous surface fastener tape of the ninth embodiment.
Figure 28:
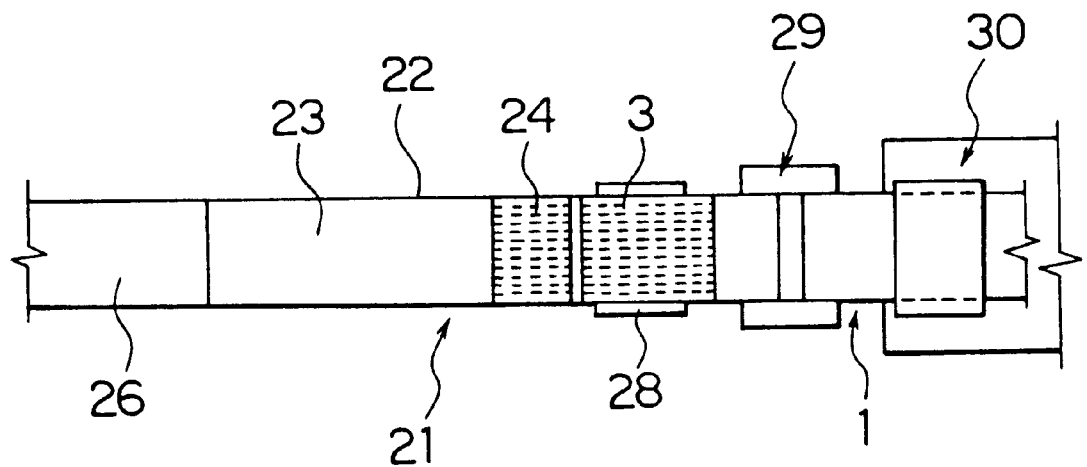
FIG. 28 is a fragmentary plan view of the injection molding machine of FIG. 27.
Figure 29:
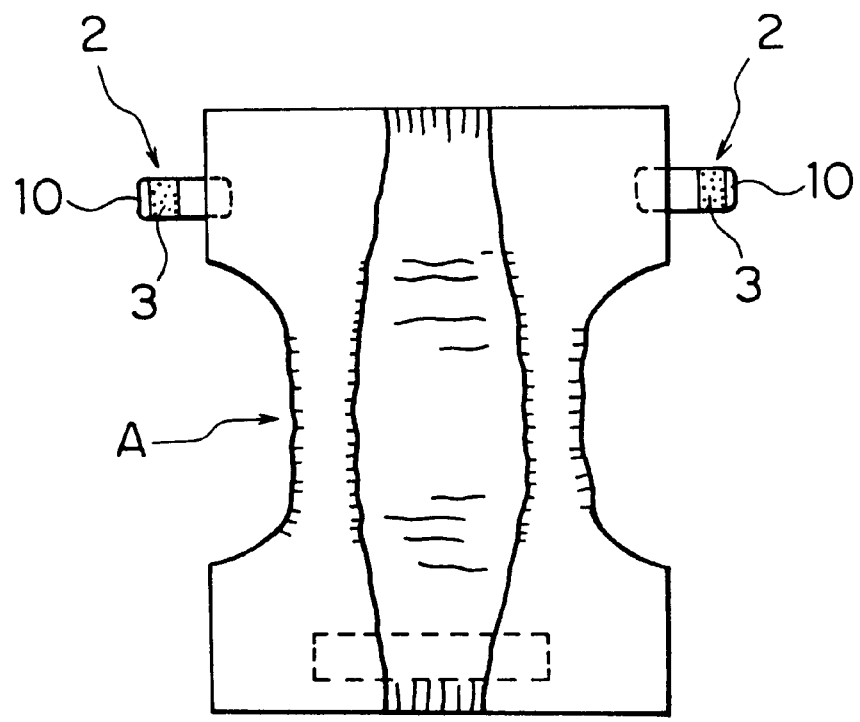
FIG. 29 is a plan view of a paper diaper in which surface fastener pieces obtained from the continuous surface fastener tape of this invention are used.
Figure 30:
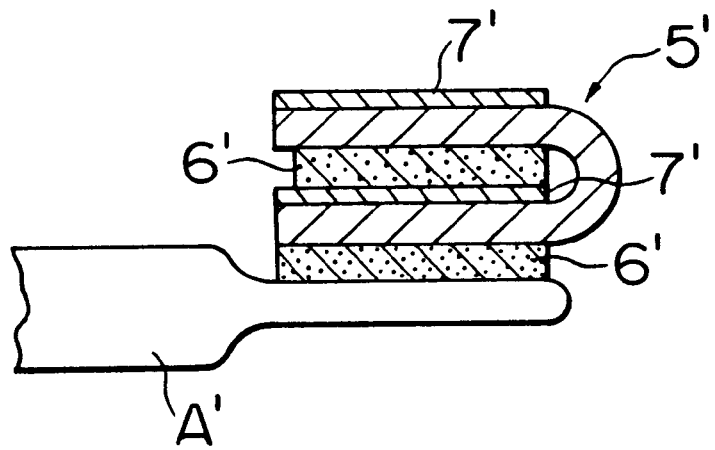
FIG. 30 is a fragmentary cross-sectional view of a conventional surface fastener used in a paper diaper.
Figure 31:
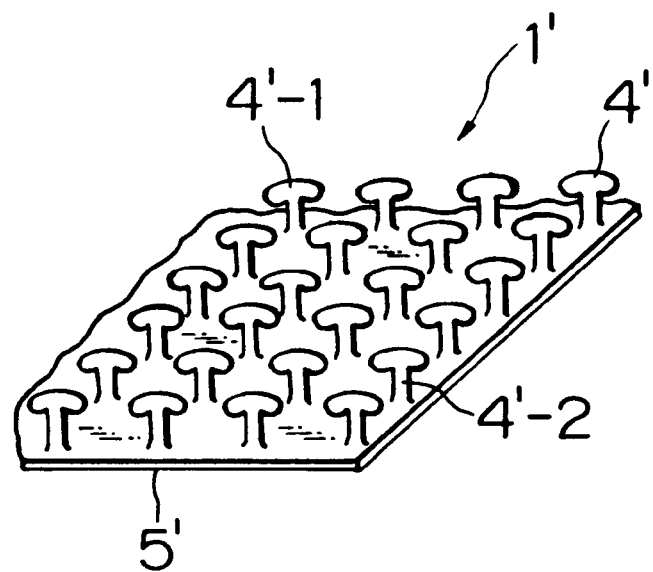
FIG. 31 is a fragmentary perspective view of another conventional surface fastener to be used in a diaper.

In the manufacturing method for the surface fastener tape 1 of FIGS. 24 and 25, having a succession of male engaging portions 3 molded on the front surface of a continuous-length substrate sheet 5 at regular distances along its entire length, and a succession of adhesive layers 6 are arranged on the front surface of the substrate sheet 5 one at a position off to each of the male engaging portions 3, a continuous-type injection molding machine 21 of FIGS. 27 and 28 is used. In the injection molding machine 21, a die wheel 22 has in its circumferential surface a number of circumferentially regularly spaced engaging-portion-forming sections 25, each composed of a multiplicity of engaging-element-forming cavities 24 and extending through the entire width of the die wheel 22, and a number of circumferentially spaced substrate-sheet-forming shallow recesses 23 extending along the entire width of the die wheel 22. An injection nozzle 26 having a sprue 27 is disposed to confront the circumferential surface of the die wheel 22 for injecting molten resin to the die wheel 22. A guide roller 28 is disposed diametrically opposite to the injection nozzle 26 with respect to the die wheel 22. Downstream of the guide roller 28, an adhesive agent applicator 29 is disposed for applying an adhesive agent to the front surface of the substrate sheet 5 through the entire width. Downstream of the adhesive agent applicator 29, a peel paper attaching device 30 is disposed for attaching peel papers 7 successively to the entire area of the adhesive layers 6 along the entire width of the substrate sheet 5 in synchronism with the spraying action of the adhesive agent applicator 29. A pair of drawing rollers are disposed downstream of the peel paper attaching device 30 for drawing and discharging the substrate sheet 5 to store the continuous surface fastener tape 1 in roll. The surface fastener tape 1 is cut into individual surface fastener pieces 2 which are attached to the diapers A during the diaper production.

In manufacturing this surface fastener tape 1, in the first step, molten resin is injected to the circumferential surface of the die wheel 22 from the injection nozzle 26 via the sprue 27 to integrally mold a continuous surface fastener tape 1 in which the flat parts of the substrate sheet 5 and the engaging portion 3 are arranged alternately at a predetermined distances along the entire length. The molded surface fastener tape 1 is removed off the die wheel 22 by the guide roller 28.

In the second step, successive adhesive layers 6 which are formed next to the preceding engaging portion 3 by applying adhesive agent by the adhesive agent applicator 29 along the entire width of the substrate sheet 5 are arranged on the front surface of the substrate sheet 5 at regular distances in such a manner that each adhesive layer 6 is disposed off to the respective preceding male engaging portion 3 with an appropriate space to the following engaging portion 3.

In the third step, after the peel papers 7 are supplied and attached to the front surfaces of the respective adhesive layers 6, the substrate sheet 5 is drawn and discharged by the drawing rollers to store the continuous surface fastener tape 1 in roll. Then the continuous surface fastener tape 1 is cut transversely between the male engaging portion 3 and the adjacent adhesive layer 6 to provide an individual surface fastener piece 2 for attachment to the diaper A during the diaper production.

In the foregoing embodiments, the method and the apparatus for injection molding are described. Alternatively they may be adopted in extrusion molding also.

With the continuous surface fastener tape and the manufacturing method according to this invention, following advantages results can be achieved:

According to the first aspect of the invention, since the surface fastener is manufactured by a method comprising continuously molding a male engaging portion 3 integrally on part of a continuous-length flat substrate sheet 5 of thermoplastic resin to obtain a continuous surface fastener tape 1, applying an adhesive agent to the substrate sheet 5 at a region apart from the male engaging portion 3 to form an adhesive layer 6, and storing the resulting continuous surface fastener tape 1 in superposed form so that the continuous surface fastener tape 1 may be cut into individual surface fastener pieces 2, it is possible to attach and use the individual surface fastener pieces 2 to diapers simply and to store easily in continuous shape. Since a necessary volume of individual surface fastener pieces 2 can be cut off the continuous surface fastener tape 1 as the demand arises, simple stock management can be achieved to improve the rate of production of diapers.

According to the second and third aspects of the invention, since the male engaging portion 3 and the adhesive layer 6 are arranged on the same surface or opposite surfaces of the substrate sheet 5, it is possible to cope with various types of diapers so that the individual surface fastener pieces 2, if cut off the continuous surface fastener tape 1, can be attached easily.

According to the fourth aspect of the invention, since the adhesive layer 6 in the form of a double-sided adhesive tape 9 having a pair of adhesive layers one at each side is attached onto the surface of the substrate sheet 5, it is possible to form the adhesive layer 6 which can attach the individual surface fastener piece 2 to a paper diaper in a simple action.

According to the fifth aspect of the invention, partly since a single male engaging portion 3 is molded centrally and longitudinally on one surface of the substrate sheet 5 and partly since two adhesive layers 6 are formed on the same surface of the substrate sheet along opposite longitudinal margins with a space from the male engaging portion 3, it is possible to obtain various shapes of individual surface fastener pieces 2 to meet with different types of paper diapers simply.

According to the sixth aspect of the invention, since a peel paper is attached to the outer surface of the adhesive layer 6 on the substrate sheet 5, it is possible to store the continuous surface fastener tape 1 in a stabilized form until it is used in paper diapers, realizing easy handling of the surface fastener tape 1.

According to the seventh aspect of the invention, since the part of the substrate sheet 5 having engaging portion 3 and the remaining flat part of the substrate sheet 5 are molded using different kinds of thermoplastic resins in such a manner that the flat part of the substrate sheet 5 is more elastic than the engaging-element-existing part to make the individual surface fastener pieces 2 expandable/contractible, it is possible to facilitate using the individual surface fastener pieces 2 in paper diapers.

According to the eighth, ninth, tenth and eleventh aspects of the invention, partly since the surface fastener tape 1 is molded at once using thermoplastic resin and partly since the adhesive layer 6 is formed on the molded surface fastener tape 1 simply, it is easy to manufacture the continuous surface fastener tape 1 enabling simple stock management. It is also possible to manufacture the continuous surface fastener tape 1 in which the male engaging portion 3 and the adhesive layer 6 are arranged on the substrate sheet 5 with a space from one another, and further the surface fastener tape 1 having peel papers 7 attached on the adhesive layers 6 which is easy to handle. Further it is possible to form the adhesive layer 6 simply using a double-sided adhesive tape 9 and to manufacture the surface fastener tape 1 in which the male engaging portions 3 and the adhesive layers 6 are arranged on the substrate sheet 5 alternately along its entire length.

According to the twelfth aspect of the invention, since the male engaging portion 3 is molded on the substrate sheet 5 off to one longitudinal edge in the first step, it is possible to manufacture the continuous surface fastener tape, which is adapted to be cut along transverse cutting lines to obtain individual surface fastener pieces 2, in a very simple process.

According to the thirteenth aspect of the invention, since a single male engaging portion 3 is molded centrally on the substrate sheet 5 in the first step and two adhesive layers 6 are formed on opposite longitudinal margins of the substrate sheet 5 in the second step, it is possible to manufacture the continuous surface fastener tape 1, from which various shapes of individual surface fastener pieces 2 can be obtained, in a very simple manner.

According to the fourteenth and fifteenth aspects of the invention, partly since the part of the substrate sheet 5 having the engaging portion 3 and the remaining flat part of the substrate sheet 5 are molded in the first step using different kinds of thermoplastic resins in such a manner that the flat part of the substrate sheet 5 is more elastic than the engaging-element-existing part, and partly since the part of the substrate sheet 5 having the engaging portion 3 and the part of the substrate sheet 5 having the adhesive layer 6 are molded of the same kind of thermoplastic resin and the flat part of the substrate sheet 5 between the engaging-element-existing part and the adhesive-layer-existing part is molded of a different kind of thermoplastic resin in such a manner that the flat part of the substrate sheet 5 is more elastic to make part of the individual surface fastener piece expandable/contractible, it is possible to manufacture an easy-to-use surface fastener tape 1 in a simple process.

According to the sixteenth aspect of the invention, partly since a non-woven cloth 8 is attached to the engaging-element-free flat surface of the substrate sheet 5, and partly since an adhesive layer 6 is provided to the non-woven cloth 8 at its one surface confronting the front surface of the substrate sheet 5, it is possible to obtain a surface fastener pieces 2 excellent in touch in a simple process.

What is claimed is:

1. A surface fastener sheet comprising:
   (a) a continuous length of flat substrate sheet of thermoplastic resin having a width sufficient for forming a surface fastener piece;
   (b) a male engaging portion molded integrally on part of said substrate sheet; and
   (c) an adhesive layer formed of an adhesive agent applied to part of said substrate sheet and spaced from said male engaging portion;
   (d) said surface fastener sheet being adapted to be stored in superposed form and to be cut into the individual surface fastener pieces.

2. A surface fastener tape according to claim 1, wherein part of said substrate sheet having said engaging portion and the remaining flat part of said substrate sheet are molded using different kinds of thermoplastic resins in such a manner that said remaining flat part is more elastic than said part having said engaging portion.

3. A surface fastener tape according to claim 2, wherein said male engaging portion and said adhesive layer are arranged on the same surface of said substrate sheet.

4. A surface fastener tape according to claim 2, wherein said male engaging portion and said adhesive layer are arranged one on each of opposite surfaces of said substrate sheet.

5. A surface fastener tape according to claim 2, wherein said adhesive layer includes a double sided adhesive tape adhered to part of said substrate sheet.

6. A surface fastener tape according to claim 2, wherein said adhesive layer includes a peel paper attached to an outer surface of said adhesive layer.

7. A surface fastener tape according to claim 1, wherein said male engaging portion and said adhesive layer are arranged on the same surface of said substrate sheet.

8. A surface fastener tape according to claim 7, wherein said adhesive layer Includes a double-sided adhesive tape adhered to part of said substrate sheet.

9. A surface fastener tape according to claim 7, wherein said male engaging portion is molded centrally and longitudinally on said substrate sheet, and said adhesive layer is a double form composed of two adhesive layer s arranged one on each of opposite outer margins of said substrate sheet.

10. A surface fastener tape according to claim 7, wherein said adhesive layer includes a peel paper attached to an outer surface of said adhesive layer.

11. A surface fastener tape according to claim 1, wherein said male engaging portion and said adhesive layer are arranged one on each of opposite surfaces of said substrate sheet.

12. A surface fastener tape according to claim 11, wherein said adhesive layer includes a double-sided adhesive tape adhered to part of said substrate sheet.

13. A surface fastener tape according to claim 11, wherein said male engaging portion is molded centrally and longitudinally on said substrate sheet, and said adhesive layer is a double form composed of two adhesive layers arranged one on each of opposite outer margins of said substrate sheet.

14. A surface fastener tape according to claim 11, wherein said adhesive layer includes a peel paper attached to an outer surface of said adhesive layer.

15. A surface fastener tape according to claim 1, wherein said adhesive layer includes a double-sided adhesive tape adhered to part of said substrate sheet.

16. A surface fastener tape according to claim 1, wherein said adhesive layer includes a peel paper attached to an outer surface of said adhesive layer.

* * * * *